United States Patent
Karasawa

(10) Patent No.: US 9,730,722 B2
(45) Date of Patent: Aug. 15, 2017

(54) LIQUID EJECTION CONTROL DEVICE, LIQUID EJECTION SYSTEM, AND CONTROL METHOD

(71) Applicant: SEIKO EPSON CORPORATION, Tokyo (JP)

(72) Inventor: Junichi Karasawa, Shimosuwa-machi (JP)

(73) Assignee: SEIKO EPSON CORPORATION, Tokyo (JP)

(*) Notice: Subject to any disclaimer, the term of this patent is extended or adjusted under 35 U.S.C. 154(b) by 24 days.

(21) Appl. No.: 15/009,539

(22) Filed: Jan. 28, 2016

(65) Prior Publication Data

US 2016/0221335 A1 Aug. 4, 2016

(30) Foreign Application Priority Data

Feb. 2, 2015 (JP) ................................. 2015-018187

(51) Int. Cl.
| | |
|---|---|
| *B41J 2/045* | (2006.01) |
| *A61B 17/3203* | (2006.01) |
| *A61B 17/3205* | (2006.01) |
| *A61B 17/00* | (2006.01) |

(Continued)

(52) U.S. Cl.
CPC ...... *A61B 17/3203* (2013.01); *A61B 17/3205* (2013.01); *B41J 2/04581* (2013.01); *B41J 2/04588* (2013.01); *A61B 90/96* (2016.02); *A61B 2017/00154* (2013.01); *A61B 2017/00181* (2013.01); *A61B 2017/00194* (2013.01); *A61B 2017/00473* (2013.01); *A61B 2017/00482* (2013.01); *A61B 2090/0818* (2016.02)

(58) Field of Classification Search
CPC ............ A61B 17/3203; A61B 17/3205; A61B 2017/00473; A61B 2017/00154; A61B 90/96; A61B 2090/0818; A61B 2017/00194; A61B 2017/00181; A61B 2017/00482; B41J 2/04588; B41J 2/04581
See application file for complete search history.

(56) References Cited

U.S. PATENT DOCUMENTS

| | | |
|---|---|---|
| 2010/0069937 A1 | 3/2010 | Seto et al. |
| 2013/0096601 A1 | 4/2013 | Asahi |

FOREIGN PATENT DOCUMENTS

| | | |
|---|---|---|
| EP | 2 286 745 A2 | 2/2011 |
| JP | 2005-152127 A | 6/2005 |

(Continued)

OTHER PUBLICATIONS

European Search Report dated Jun. 14, 2016 as received in Application No. 16153342.7.

*Primary Examiner* — Julian Huffman
(74) *Attorney, Agent, or Firm* — Maschoff Brennan

(57) ABSTRACT

In a liquid ejection control device, an ejection tube section type acquisition unit discriminates an ejection tube section type of an ejection tube section mounted in a main body section, and acquires a fitted correspondence relationship fitting the discriminated ejection tube section type. A voltage amplitude setting unit sets a voltage amplitude of a drive voltage waveform so as to cause momentum to meet a momentum instruction value input by using a momentum dial based on a rising index value related to rising of the drive voltage waveform and a repetitive frequency instruction value input by using a repetitive frequency dial with reference to the fitted correspondence relationship.

19 Claims, 20 Drawing Sheets

(51) Int. Cl.
  *A61B 90/96* (2016.01)
  *A61B 90/00* (2016.01)

(56) References Cited

FOREIGN PATENT DOCUMENTS

JP  2013-085640 A  5/2013
JP  2013-085865 A  5/2013

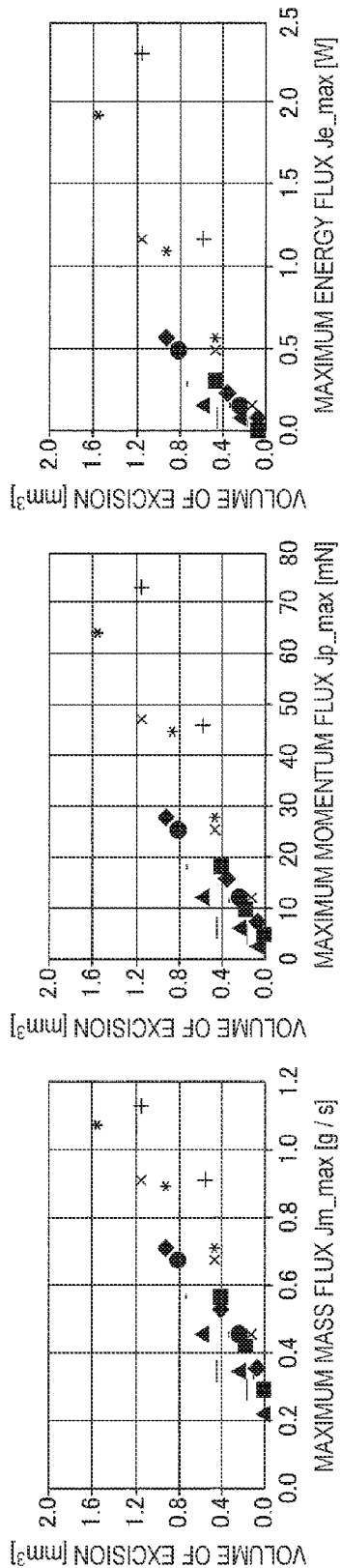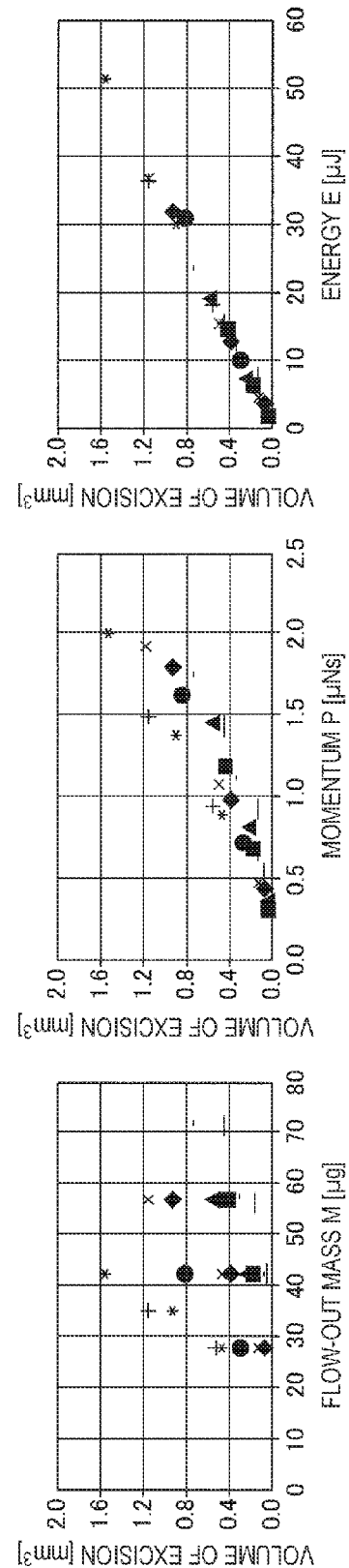
FIG. 7A, FIG. 7B, FIG. 7C, FIG. 7D, FIG. 7E, FIG. 7F

| EJECTION TUBE SECTION ID | DIAL POSITION OF REPETITIVE FREQUENCY | INSTRUCTION VALUE OF REPETITIVE FREQUENCY | DIAL POSITION OF MOMENTUM | INSTRUCTION VALUE OF MOMENTUM | VOLTAGE AMPLITUDE | RISING FREQUENCY |
|---|---|---|---|---|---|---|
| ID_001 | 1 | F_001 | 1 | P_001 | V_011 | |
| | | | 2 | P_002 | V_012 | |
| | | | 3 | P_003 | V_013 | |
| | | | 4 | P_004 | V_014 | |
| | | | 5 | P_005 | V_015 | |
| | 2 | F_002 | 1 | P_001 | V_021 | |
| | | | 2 | P_002 | V_022 | |
| | | | 3 | P_003 | V_023 | |
| | | | 4 | P_004 | V_024 | |
| | | | 5 | P_005 | V_025 | |
| | 3 | F_003 | 1 | P_001 | V_031 | f_001 |
| | | | 2 | P_002 | V_032 | |
| | | | 3 | P_003 | V_033 | |
| | | | 4 | P_004 | V_034 | |
| | | | 5 | P_005 | V_035 | |
| | 4 | F_004 | 1 | P_001 | V_041 | |
| | | | 2 | P_002 | V_042 | |
| | | | 3 | P_003 | V_043 | |
| | | | 4 | P_004 | V_044 | |
| | | | 5 | P_005 | V_045 | |
| | 5 | F_005 | 1 | P_001 | V_051 | |
| | | | 2 | P_002 | V_052 | |
| | | | 3 | P_003 | V_053 | |
| | | | 4 | P_004 | V_054 | |
| | | | 5 | P_005 | V_055 | |

| EJECTION TUBE SECTION ID | SHAPE CONDITION | WEIGHT CONDITION |
|---|---|---|
| ID_001 | XXXX  | XXXX |
| ID_002 | XXXX  | XXXX |
| ID_003 | XXXX  | XXXX |
| ID_004 | XXXX  | XXXX |
| ⋮ | ⋮ | ⋮ |

FIG. 19

| EJECTION TUBE SECTION ID | DIAL POSITION OF REPETITIVE FREQUENCY | INSTRUCTION VALUE OF REPETITIVE FREQUENCY | DIAL POSITION OF MOMENTUM | INSTRUCTION VALUE OF MOMENTUM | DIAL POSITION OF RISING FREQUENCY | INSTRUCTION VALUE OF RISING FREQUENCY | VOLTAGE AMPLITUDE |
|---|---|---|---|---|---|---|---|
| ID_001 | 1 | F_011 | 1 | P_011 | 1 | f_011 | V_111 |
| | | | | | 2 | f_012 | V_112 |
| | | | | | 3 | f_013 | V_113 |
| | | | | | 4 | f_014 | V_114 |
| | | | | | 5 | f_015 | V_115 |
| | | | 2 | P_012 | 1 | f_011 | V_121 |
| | | | | | 2 | f_012 | V_122 |
| | | | | | 3 | f_013 | V_123 |
| | | | | | 4 | f_014 | V_124 |
| | | | | | 5 | f_015 | V_125 |
| | | | ... | ... | ... | ... | ... |
| | | | 5 | P_015 | 1 | f_011 | V_151 |
| | | | | | 2 | f_012 | V_152 |
| | | | | | 3 | f_013 | V_153 |
| | | | | | 4 | f_014 | V_154 |
| | | | | | 5 | f_015 | V_155 |
| | 2 | F_012 | 1 | P_011 | 1 | f_011 | V_211 |
| | | | | | 2 | f_012 | V_212 |
| | | | | | 3 | f_013 | V_213 |
| | | | | | 4 | f_014 | V_214 |
| | | | | | 5 | f_015 | V_215 |
| | | | ... | ... | ... | ... | ... |
| | | | 5 | P_015 | 1 | f_011 | V_251 |
| | | | | | 2 | f_012 | V_252 |
| | | | | | 3 | f_013 | V_253 |
| | | | | | 4 | f_014 | V_254 |
| | | | | | 5 | f_015 | V_255 |
| | ... | ... | ... | ... | ... | ... | ... |

LIQUID EJECTION CONTROL DEVICE, LIQUID EJECTION SYSTEM, AND CONTROL METHOD

BACKGROUND

1. Technical Field

The present invention relates to a liquid ejection control device and the like which control a liquid ejection device ejecting a liquid in a pulsed state by using a piezoelectric element.

2. Related Art

There is a known technology in which a liquid is ejected in a pulsed state and an excision target is excised. Ejection of a pulsed liquid is a jet flow of the liquid which is ejected from a nozzle in a pulsating manner and will be appropriately referred to as "a pulsed liquid jet" in this specification.

There are various purposes of the pulsed liquid jet. For example, JP-A-2005-152127 discloses a proposed technology in which the pulsed liquid jet is utilized for a surgical operation in the medical field. In this case, the excision target is a living tissue, and the liquid is a physiological salt solution.

As a mechanism which generates a pulsed liquid jet, there is a known mechanism in which a piezoelectric element is used. In the mechanism, the piezoelectric element generates an instantaneous pressure in an operation fluid (a fluid) so as to cause a liquid to be ejected in a pulsed state by adding a drive voltage in a pulse wave shape to the piezoelectric element. Accordingly, when varying the strength of the pulsed liquid jet, the drive voltage applied to the piezoelectric element is controlled. Therefore, it is possible to consider a specification in which the strength of the pulsed liquid jet becomes variable by instructing a characteristic value of a drive voltage applied to the piezoelectric element, for example, the amplitude of a drive voltage waveform (which is a voltage amplitude and can also be referred to as the magnitude of a drive voltage) through an operation unit such as an operation dial or an operation button.

However, it is found that even though the characteristic value of the drive voltage to be instructed through the operation unit is changed, there may be a case where excisional circumstances such as the depth of excision and the volume of excision of the excision target cannot be changed as intended by a user. Detailed description will be given below. However, for example, it is found that even though a user changes the voltage amplitude twice, four times, ½, or ¼, the depth of excision and the volume of excision do not necessarily change in the same manner. When the pulsed liquid jet is used for the purpose of a surgical operation, it is not possible for an operator to obtain an operational effect in accordance with the feeling of the operation, thereby causing the possibility of a problem.

Meanwhile, when a cycle of ejecting a pulsed liquid jet is caused to be variable, the depth of excision and the volume of excision per unit time can be increased and reduced so that the velocity of excising the excision target becomes adjustable. However, the strength and the like of the pulsed liquid jet for one pulse can be changed based on the fact that when the cycle of ejection is changed, the shape of the drive voltage waveform changes. Therefore, there may be a case where the excision speed proportional to the frequency of ejection as intended by a user cannot be obtained even though the depth of excision and the volume of excision caused by the pulsed liquid jet for one pulse are changed before and after the cycle of ejection is changed, and the cycle of ejection is shortened, that is, the frequency of ejection is raised.

In addition, for example, in a case of the purpose of a surgical operation, a plurality types of liquid ejection devices in each of which an ejection tube portion where a liquid passes through has the shape, the length, the tube diameter, the material, the diameter of a nozzle, or the like different from each other are classified in accordance with the circumstances of a surgical operation, a resection site, or the like. Therefore, the depth of excision and the volume of excision caused by the pulsed liquid jet for one pulse can be changed in accordance with the type of the ejection tube portion of the liquid ejection device in use.

SUMMARY

An advantage of some aspects of the invention is to propose a technique in which the strength of a pulsed liquid jet can be set so as to meet the intention of a user and the user-friendliness thereof is improved.

A first aspect of the invention is directed to a liquid ejection control device which applies a given drive voltage waveform to a piezoelectric element and controls ejection of a pulsed liquid jet from a liquid ejection device which ejects a liquid in a pulsed state by using the piezoelectric element. The liquid ejection device has an ejection tube section in which an ejection port of the liquid is formed and which is configured to be attachable/detachable with respect to a main body section including the piezoelectric element. The liquid ejection control device includes a type discrimination unit that discriminates an ejection tube section type of the ejection tube section; a correspondence relationship acquisition unit that acquires a fitted correspondence relationship which fits the discriminated ejection tube section type from correspondence relationships that are set for each of the ejection tube section types while the correspondence relationship is based on a first instruction value related to momentum of the pulsed liquid jet, a second instruction value related to the number of times of ejection of the pulsed liquid jet per unit time, and an index value related to a voltage amplitude of the drive voltage waveform and rising of the drive voltage waveform; a first operation unit that inputs the first instruction value; a second operation unit that inputs the second instruction value; and a voltage amplitude setting unit that sets the voltage amplitude of the drive voltage waveform so as to cause the momentum to meet the first instruction value with reference to the fitted correspondence relationship based on the index value and the second instruction value.

As another aspect of the invention, the invention can be configured as a control method of applying a given drive voltage waveform to a piezoelectric element and controlling ejection of a pulsed liquid jet from a liquid ejection device which ejects a liquid in a pulsed state by using the piezoelectric element. The liquid ejection device has an ejection tube section in which an ejection port of the liquid is formed and which is configured to be attachable/detachable with respect to a main body section including the piezoelectric element. The control method includes discriminating an ejection tube section type of the ejection tube section; acquiring a fitted correspondence relationship which fits the discriminated ejection tube section type from correspondence relationships that are set for each of the ejection tube section types while the correspondence relationship is based on a first instruction value related to momentum of the pulsed liquid jet, a second instruction value related to the number of times of ejection of the pulsed liquid jet per unit time, and an index value related to voltage amplitude of the drive voltage waveform and rising of the drive voltage waveform; inputting the first instruction value; inputting the second instruction value; and setting the voltage amplitude of the drive voltage waveform so as to cause the momentum to meet the first instruction value with reference to the fitted correspondence relationship based on the index value and the second instruction value.

As described below, the depth of excision and the volume of excision performed by the pulsed liquid jet are highly related with the momentum of the pulsed liquid jet. Meanwhile, the relationship of the depth of excision and the volume of excision with the momentum may vary in accordance with the type of the ejection tube portion of the liquid ejection device. According to the first aspect and the like of the invention, the ejection tube section type of the ejection tube section mounted in the main body section is discriminated, and a fitted correspondence relationship which is set regarding the ejection tube section type is acquired. When the first instruction value related to the momentum of the pulsed liquid jet and the second instruction value related to the number of times of ejection of the pulsed liquid jet per unit time are input, the voltage amplitude of the drive voltage waveform is set so as to cause the momentum to meet the first instruction value in accordance with the fitted correspondence relationship based on the index value of the drive voltage waveform and the second instruction value. Accordingly, even though the type of the ejection tube section varies, it is possible to realize the depth of excision and the volume of excision answering the intention of a user and feeling of the operation by directly instructing the momentum of the pulsed liquid jet. Thus, the user-friendliness thereof can be improved.

Since the number of times of ejection of the pulsed liquid jet per unit time can be instructed, it is possible to increase and reduce the number of times of ejection while the first instruction value is maintained, for example. Therefore, it is possible to adjust an excision speed without changing the depth of excision and the volume of excision caused by the pulsed liquid jet for one pulse before and after the number of times of ejection is changed. Thus, an improvement of the user-friendliness thereof can be achieved.

A second aspect of the invention is directed to the liquid ejection control device according to the first aspect of the invention, in which the ejection tube section has a first retainer which retains type information of the ejection tube section, and the type discrimination unit acquires the type information from a read-out result of a first reader reading out retained information from the first retainer and may discriminate the ejection tube section type.

According to the second aspect of the invention, it is possible to discriminate the ejection tube section type of the ejection tube section mounted in the main body section by acquiring the type information of the ejection tube section from the first retainer which is included in the ejection tube section.

A third aspect of the invention is directed to the liquid ejection control device according to the first aspect of the invention, in which the type discrimination unit acquires at least any one of shape information and weight information of the ejection tube section and discriminates the ejection tube section type.

According to the third aspect of the invention, it is possible to discriminate the ejection tube section type of the ejection tube section mounted in the main body section by acquiring the shape information or the weight information of the ejection tube section.

A fourth aspect of the invention is directed to the liquid ejection control device according to any of the first to third aspects of the invention, in which the ejection tube section has a second retainer which retains the fitted correspondence relationship fitting the ejection tube section type of the ejection tube section, and the correspondence relationship acquisition unit acquires the fitted correspondence relationship from a read-out result of a second reader reading out retained information from the second retainer.

According to the fourth aspect of the invention, it is possible to acquire the fitted correspondence relationship fitting the ejection tube section type of the ejection tube section mounted in the main body section from the second retainer which is included in the ejection tube section.

A fifth aspect of the invention is directed to the liquid ejection control device according to any of the first to fourth aspects of the invention, which further includes a third operation unit that inputs a third instruction value related to the index value.

According to the fifth aspects of the invention, it is possible to input the third instruction value related to the index value of the drive voltage waveform.

A sixth aspect of the invention is directed to the liquid ejection control device according to any of the first to fifth aspects of the invention, which further includes a falling shape setting unit that variably sets a falling shape of the drive voltage waveform in accordance with the second instruction value.

According to the sixth aspect of the invention, it is possible to control repetitive ejection of the pulsed liquid jet by variably setting the falling shape of the drive voltage waveform so as to cause the number of times of ejection of the pulsed liquid jet per unit time to meet the second instruction value while a predetermined or desired rising shape of the drive voltage waveform is maintained.

A seventh aspect of the invention is directed to the liquid ejection control device according to any of the first to sixth aspects of the invention, which further includes a display control unit that performs controlling to display at least one of the first instruction value and the second instruction value.

According to the seventh aspect of the invention, it is possible to display at least one of the first instruction value related to the momentum of the pulsed liquid jet and the second instruction value related to the number of times of ejection of the pulsed liquid jet per unit time. Accordingly, it is possible to visually check the current momentum of the pulsed liquid jet instructed by a user, the index indicating the number of times of ejection per unit time, and the like. Therefore, the user-friendliness thereof can be further improved.

An eighth aspect of the invention is directed to the liquid ejection control device according to any of the first to seventh aspects of the invention, in which the liquid ejection device having momentum of the pulsed liquid jet within a range from 2 [nano-newton seconds (nNs)] to 2 [milli-newton seconds (mNs)] or having the kinetic energy within a range from 2 [nano-joules (nJ)] to 200 [milli-joules (mJ)] is controlled.

According to the eighth aspect of the invention, it is possible to control the liquid ejection device having the momentum of the pulsed liquid jet within the range from 2 [nNs] to 2 [mNs] or having the kinetic energy within a range from 2 [nJ] to 200 [mJ]. Accordingly, for example, it is suitable for excising soft materials such as living tissues, foods, a gel material, and resin materials such as rubber and plastic.

A ninth aspect of the invention is directed to the liquid ejection control device according to any of the first to eighth aspects of the invention, in which the liquid ejection device which excises a living tissue by using the pulsed liquid jet is controlled.

According to the ninth aspect of the invention, it is possible to control the strength of the pulsed liquid jet which is suitable for the purpose of a surgical operation, for example.

A tenth aspect of the invention is directed to a liquid ejection system including the liquid ejection control device according to any of the first to ninth aspects of the invention, a liquid ejection device, and a liquid delivery pump device.

According to the tenth aspect of the invention, it is possible to realize the liquid ejection system which exhibits the operational effects of the above-described aspects of the invention.

BRIEF DESCRIPTION OF THE DRAWINGS

The invention will be described with reference to the accompanying drawings, wherein like numbers reference like elements.

FIGS. 7A to 7F are diagrams illustrating simulation results (volume of excision).

FIG. 14 is a diagram illustrating an example of a data configuration of an momentum conversion table in Exemplary Embodiment 1.

FIG. 19 is a diagram illustrating an example of a data configuration of an momentum conversion table in Exemplary Embodiment 2.

DESCRIPTION OF EXEMPLARY EMBODIMENTS

Figure 1:
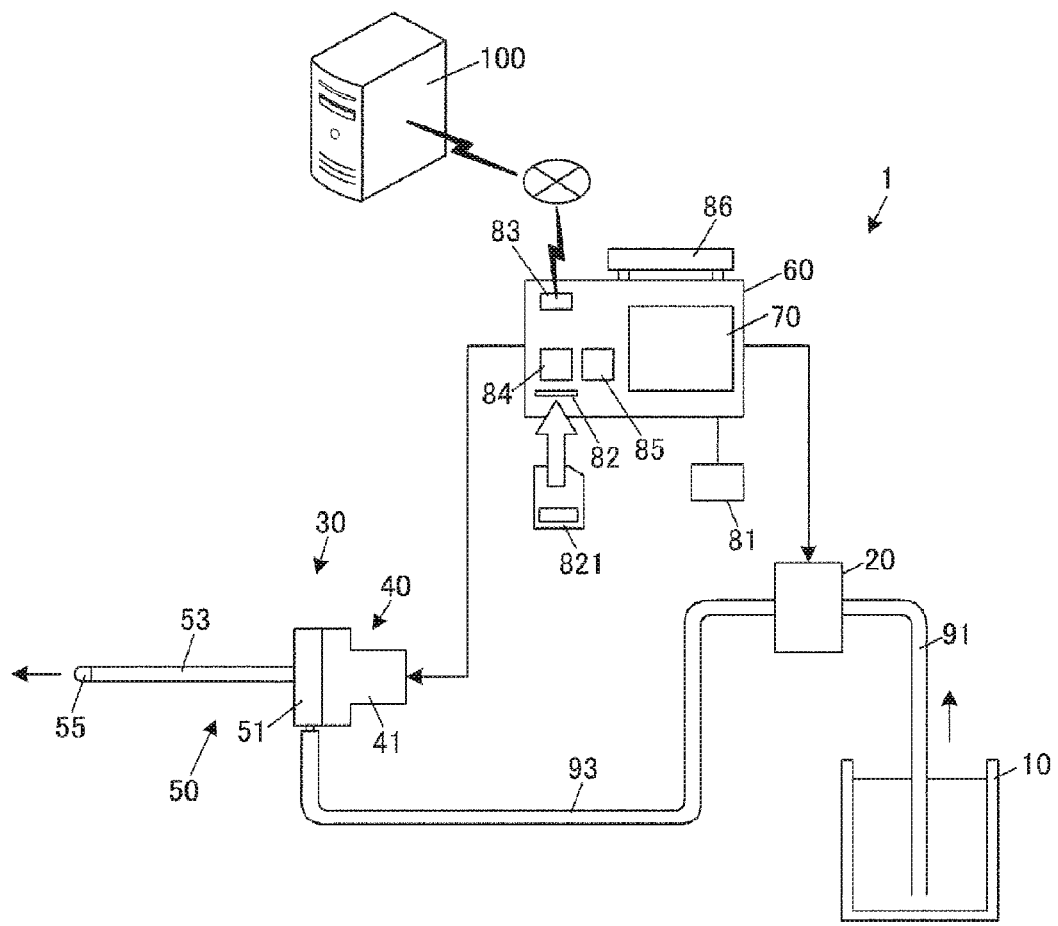
FIG. 1 is a diagram illustrating an example of the overall configuration of a liquid ejection system.

Hereinafter, an embodiment of a liquid ejection control device, a liquid ejection system, and a control method according to the invention will be described. The invention is not limited by the embodiment described below, and a form to which the invention can be applied is not also limited by the below-referenced embodiment. In the disclosed drawings, the same reference numerals and signs are applied to the same portions.

Overall Configuration

FIG. 1 is a diagram illustrating an example of the overall configuration of a liquid ejection system 1 in the embodiment. The liquid ejection system 1 is used for the purpose of processing a soft material, for example, a surgical operation while having living tissues as an excision target, processing of foods while having foods as an excision target, processing of gel materials, and excision of resin materials such as rubber and plastic. The liquid ejection system 1 ejects a pulsed liquid jet of which the momentum ranges from 2 [nano-newton seconds (nNs)] to 2 [milli-newton seconds (mNS)] or the kinetic energy ranges from 2 [nano-joules (nJ)] to 200 [milli-joules (mJ)], thereby excising the excision target. Hereinafter, a case where incision, resection, or fragmentation of a lesion site (living tissues) (collectively referred to as "excision") is carried out will be exemplified, while the liquid ejection system 1 is used for the purpose of a surgical operation. Description will be given on the assumption that momentum flux and momentum in the embodiment indicate scalar quantity, that is, magnitude in which only the component of the pulsed liquid jet in the ejection direction is considered.

As illustrated in FIG. 1, the liquid ejection system 1 includes a container 10 which contains a liquid, a liquid delivery pump device 20, a liquid ejection device 30 which ejects a liquid in a pulsed state toward an excision target (living tissues in the embodiment), and a liquid ejection control device 60.

As operation units, the liquid ejection control device 60 includes an operation panel 70 for inputting various types of operations such as increasing/decreasing operations of momentum during a surgical operation, and an ejection pedal 81 for switching between a start and a stop of ejecting a pulsed liquid jet by being stepped on by an operator. Moreover, the liquid ejection control device 60 appropriately includes a reader/writer 82 which realizes reading and writing of data in a memory card 821, a communication device 83 for communicating with an external server apparatus 100, an image capturing device 84, a code reader 85, and a gravimeter 86.

The container 10 contains liquid such as water, a physiological salt solution, and a liquid medicine. The liquid delivery pump device 20 supplies the liquid contained in the container 10 to the liquid ejection device 30 via connection tubes 91 and 93 at predetermined pressure or a predetermined flow rate at all times.

The liquid ejection device 30 includes a main body section 40 in which a piezoelectric element 43 and the like are provided inside a main body case 41 (refer to FIG. 2), and an ejection tube section 50 in which a pipe-like ejection tube 53 is erected on a base 51. The ejection tube section 50 is configured to be attachable/detachable with respect to the main body section 40. The liquid ejection device 30 is a portion to be held and operated by an operator in one's hand (a handpiece) during a surgical operation. The liquid ejection device 30 generates a pulse flow by applying pulsation to a liquid supplied from the liquid delivery pump device 20 and eventually ejects the generated pulse flow as a pulsed liquid jet from a liquid ejection opening 551 (refer to FIG. 2) which is provided in a nozzle 55, through the ejection tube 53.

Here, as the handpiece for a surgical operation, the handpiece of which the shape of an ejection tube portion, the length, the tube diameter, the material, and the diameter of the nozzle are different from each other is prepared, and a handpiece which is suitable for the circumstances of the surgical operation, a resection site, and the like is selectively used at the time of a surgical operation. As the type of the ejection tube portion, for example, a stainless steel-made ejection tube having a length of 15 [cm], 30 [cm], or 50 [cm], or a flexible PEEK tube having a length of 1 [m], 1.5 [m], or 2 [m] can be exemplified. Regarding the shape of the ejection tube portion as well, various types of shape such as a straight line-shaped ejection tube and a bent shaped ejection tube can be exemplified. In the embodiment, the handpiece is configured to replace only the ejection tube portion with another ejection tube which is suitable for the circumstances and the like of a surgical operation by causing the ejection tube section 50 including the ejection tube 53 to be attachable/detachable with respect to the main body section 40 which includes the piezoelectric element 43 and the like while the piezoelectric element 43 for generating the pulse flow is shared. In more detail, an ejection tube section 50 is selected from various types of ejection tube sections 50 in which the configurations of the bases 51 are the same as each other and ejection tubes having the lengths, materials, and the like different from each other are erected as the ejection tube 53, in accordance with the circumstances of a surgical operation. The selected ejection tube section 50 is mounted in the main body section 40, thereby being used.

The pulse flow denotes a pulsating flow of a liquid in a state where the flow velocity or pressure of the liquid changes in a temporally significant and rapid manner. Similarly, ejection of a liquid in a pulsed state denotes pulsating ejection of a liquid in a state where the flow velocity of the liquid passing through a nozzle changes in a temporally significant manner. The embodiment exemplifies a case where a pulsed liquid jet is ejected by applying cyclic pulsation to a steady flow. However, the invention can be similarly applied to ejection of a pulsed liquid jet sporadically and intermittently performed in a state where ejection and non-ejection of a liquid are repeated.

Figure 2:
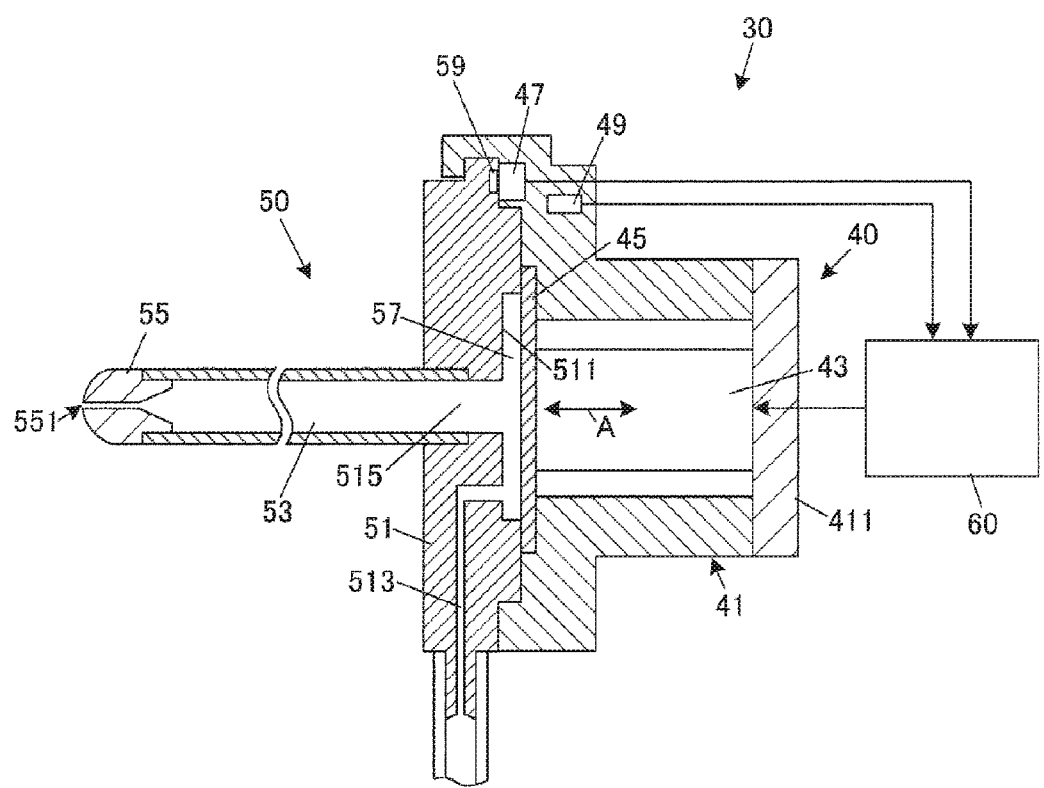
FIG. 2 is a diagram illustrating the internal structure of a liquid ejection device.

FIG. 2 is a diagram illustrating an overview of a cross-section obtained by cutting the liquid ejection device 30 along the direction of ejecting a liquid. FIG. 2 illustrates a fitting state of the main body case 41 and the base 51. The scales of the lengths and the widths of the members and portions illustrated in FIG. 2 are different from the actual scales for convenience of illustration.

The main body case 41 of the main body section 40 has a box shape of which one end is open. The piezoelectric element 43 and a diaphragm 45 for changing the volume of a pressure chamber 57 are configured to be arranged in a tubular inner space thereof. Meanwhile, on a side opposite to the side where the ejection tube 53 is erected, the base 51 of the ejection tube section 50 has a recession 511 forming the pressure chamber 57. When the ejection tube section 50 is mounted in the main body section 40 in the liquid ejection device 30, the recession 511 of the base 51 fits the opening end of the main body case 41, and the inside therebetween is sealed by a lock mechanism or the like which causes both to engage with each other. An attachment/detachment unit for the main body section 40 and the ejection tube section 50 can be appropriately selected.

The diaphragm 45 is a thin disk-shaped sheet metal, and an outer circumferential portion thereof is interposed between the main body case 41 and the base 51 so as to be fixed when being mounted in the ejection tube section 50. The piezoelectric element 43 is a lamination-type piezoelectric element, for example. One end is fixed to the diaphragm 45 between the diaphragm 45 and a bottom plate 411 of the main body case 41, and the other end is fixed to the bottom plate 411.

The pressure chamber 57 is a space which is surrounded by the diaphragm 45 and the recession 511 of the base 51. An inlet channel 513 and an outlet channel 515 which individually communicate with the pressure chamber 57 are formed on the base 51. The inner diameter of the outlet channel 515 is formed to be greater than the inner diameter of the inlet channel 513. The inlet channel 513 is connected to a connection tube 93 and introduces a liquid supplied from the liquid delivery pump device 20, to the pressure chamber 57. One end of the ejection tube 53 is connected to the outlet channel 515 and introduces a liquid flowing inside the pressure chamber 57, to the ejection tube 53. The nozzle 55 which includes the liquid ejection opening 551 having the inner diameter smaller than the inner diameter of the ejection tube 53 is inserted into the ejection tube 53 and is attached to the other end (the distal end) thereof.

The ejection tube section 50 is provided with an ejection tube side retainer 59 which is a first retainer retaining an ejection tube section ID as type information thereof allocated for an ejection tube section type of the ejection tube section 50. The main body section 40 is provided with a reader 47 which is a first reader for reading the ejection tube section ID from the ejection tube side retainer 59. The ejection tube side retainer 59 and the reader 47 are arranged respectively at appropriate places of the ejection tube section 50 and the main body section 40 so as to have a positional relationship in which the ejection tube side retainer 59 can be read by the reader 47 in the fitting state of the main body case 41 and the base 51. The ejection tube side retainer 59 is configured to be an integrated circuit (IC) tag which stores the ejection tube section ID, for example. Meanwhile, the reader 47 is configured to be an IC tag reader reading out the ejection tube section ID from the IC tag and outputs the read out ejection tube section ID to the liquid ejection control device 60. Otherwise, the ejection tube side retainer 59 may be configured to be formed by using an information code which is obtained by encoding the ejection tube section ID (for example, may be a bar code, and may also be a two-dimensional code). In this case, the reader 47 is configured to be a code reader which reads out the information code, thereby analyzing the read out information code and outputting the ejection tube section ID to the liquid ejection control device 60. The main body section 40 includes a main body side retainer 49 which is connected to the liquid ejection control device 60 through wire.

The ejection tube side retainer 59 and the reader 47 are configured to be arranged respectively in the ejection tube section 50 and the main body section 40 so as to have the positional relationship in which the reader 47 can perform reading in the fitting state of the main body case 41 and the base 51. However, as long as information stored in the IC tag can be read out, the arrangement may have a differently arranged positional relationship. For example, the arrangement may have a positional relationship in which reading can be performed at an adjacent position or in a contact state before being in the fitting state.

In the liquid ejection system 1 having the above-described configuration, a liquid contained in the container 10 is supplied to the liquid ejection device 30 by the liquid delivery pump device 20 via the connection tube 93 at predetermined pressure or a predetermined flow rate while being under the control of the liquid ejection control device 60. Meanwhile, when a drive signal is applied to the piezoelectric element 43 while being under the control of the liquid ejection control device 60, the piezoelectric element 43 expands and contracts (arrow A in FIG. 2). Since the drive signal applied to the piezoelectric element 43 is repetitively applied at a predetermined repetitive frequency (for example, several ten [Hz] to several hundred [Hz]), expansion and contraction of the piezoelectric element 43 are repeated for each cycle. Accordingly, pulsation is applied to a liquid in a steady flow flowing inside the pressure chamber 57, and a pulsed liquid jet is repetitively ejected from the liquid ejection opening 551.

Figure 3A:
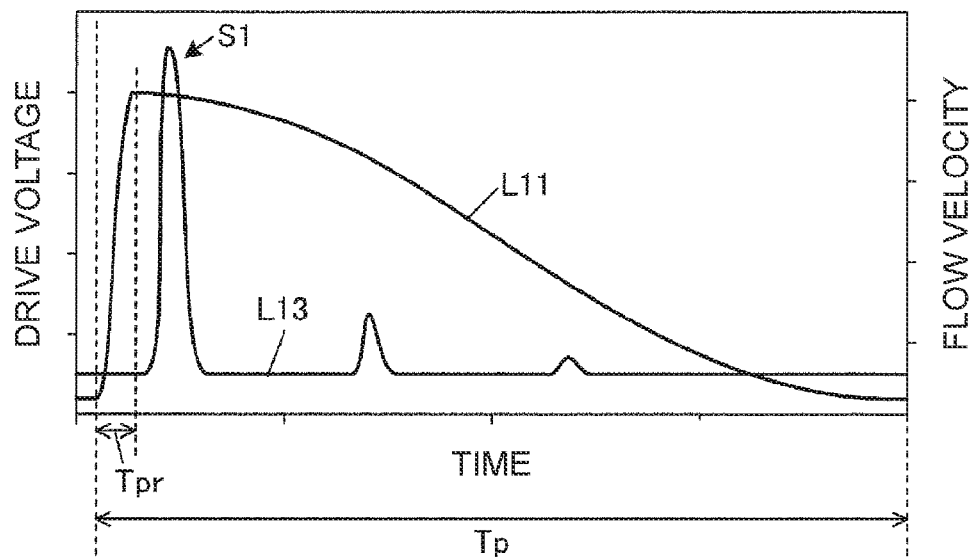
FIGS. 3A and 3B are diagrams illustrating a drive voltage waveform of a piezoelectric element in one cycle and a flow velocity waveform of a liquid at a liquid ejection opening.
Figure 3B:
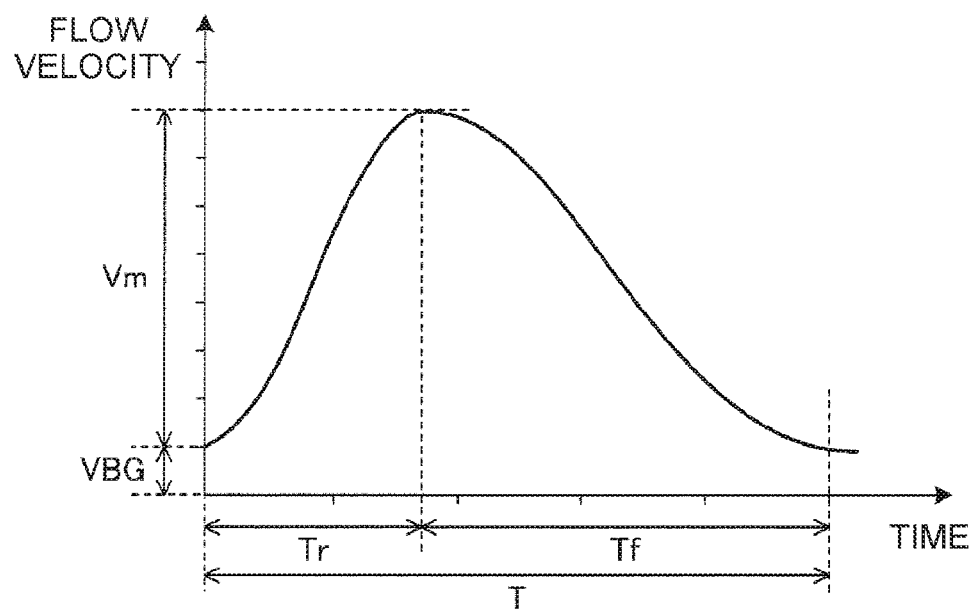

FIG. 3A is a diagram illustrating an example of a drive voltage waveform L11 of the drive signal in one cycle applied to the piezoelectric element 43. FIG. 3A also illustrates a flow velocity waveform L13 of a liquid in the liquid ejection opening 551. FIG. 3B is a diagram of a flow velocity waveform (the main peak portion) S1 which is the highest peak extracted from the peaks of the flow velocity waveform L13 illustrated in FIG. 3A.

The reference sign Tp illustrated in FIG. 3A is a repetitive cycle (a time for one cycle of the drive voltage waveform), and the reciprocal thereof is the above-described repetitive frequency. The repetitive cycle Tp ranges approximately from 1 [millisecond (ms)] to 100 [ms], and a time Tpr necessary for the drive voltage waveform to rise to the maximum voltage (a rising time) ranges approximately from 10 [microsecond (µs)] to 1000 [µs]. The repetitive cycle Tp is set to be a time longer than the rising time Tpr. When the reciprocal of the rising time Tpr is set to be the rising frequency, the repetitive frequency is set to be a frequency lower than the rising frequency. Both the rising frequency and the rising time are one of index values (rising index values) related to rising of the drive voltage.

For example, when the piezoelectric element 43 is set to expand as a positive voltage is applied, the piezoelectric element 43 rapidly expands at the rising time Tpr, and the diaphragm 45 is pressed by the piezoelectric element 43 and is thereby bent toward the pressure chamber 57 side. As the diaphragm 45 is bent toward the pressure chamber 57 side, the volume of the pressure chamber 57 is reduced, and a liquid inside the pressure chamber 57 is extruded out of the pressure chamber 57. Here, since the inner diameter of the outlet channel 515 is greater than the inner diameter of the inlet channel 513, the fluid inertance and the fluid resistance of the outlet channel 515 are smaller than the fluid resistance of the inlet channel 513. Therefore, as the piezoelectric element 43 rapidly expands, the most portion of the liquid extruded out of the pressure chamber 57 passes through the outlet channel 515 and is introduced to the ejection tube 53. Then, the extruded liquid becomes pulsed droplets, that is, a pulsed liquid jet by the liquid ejection opening 551 having the diameter smaller than the diameter of the ejection tube 53, thereby being subjected to high velocity ejection.

After having risen to the maximum voltage, the drive voltage gradually drops. In this case, the piezoelectric element 43 contracts while taking time longer than the rising time Tpr, and the diaphragm 45 is pulled by the piezoelectric element 43 so as to be bent toward the bottom plate 411 side. As the diaphragm 45 is bent toward the bottom plate 411 side, the volume of the pressure chamber 57 is increased, and a liquid is introduced to the inside of the pressure chamber 57 from the inlet channel 513.

Since the liquid delivery pump device 20 supplies a liquid to the liquid ejection device 30 at predetermined pressure or a predetermined flow rate, if the piezoelectric element 43 does not perform the expansion/contraction operation, the liquid (the steady flow) flowing in the pressure chamber 57 is introduced to the ejection tube 53 via the outlet channel 515 and is thereby ejected from the liquid ejection opening 551. Since the ejection is a liquid current at a steady velocity and a low velocity, the ejection can be referred to as a steady flow.

Principle

An essential factor as a value characterizing the pulsed liquid jet is the flow velocity waveform L13 of a jet for one pulse in the liquid ejection opening 551 illustrated in FIG. 3A together with the drive voltage waveform L11. Above all, a noteworthy factor is the main peak portion (the jet of a leading wave: S1 in FIG. 3A) of the maximum flow velocity generated immediately after the rising of the drive voltage which is extracted and illustrated in FIG. 3B. The remaining low peaks are generated due to jets which are incidentally ejected as wave of pressure fluctuation generated inside the pressure chamber 57 at the time of expansion of the piezoelectric element 43 reflectively reciprocate inside the ejection tube 53. However, the factor which determines the excisional circumstances such as the depth of excision and the volume of excision of the excision target is the jet of the leading wave (hereinafter, referred to as "the main jet") of which the flow velocity is the greatest.

Incidentally, when it is intended to change the strength of the pulsed liquid jet so as to change the depth of excision and the volume of excision of the excision target, the drive voltage waveform of the piezoelectric element 43 is controlled. Regarding controlling of the drive voltage waveform, a method performed by an operator instructing the rising frequency of the drive voltage waveform or the amplitude (the voltage amplitude) of the drive voltage waveform as the voltage characteristic value thereof can be considered. For example, a method performed by an operator instructing the rising frequency (may be the rising time Tpr) in a state where the voltage amplitude is fixed or instructing the voltage amplitude in a state where the rising frequency is fixed can be considered. It is because the voltage amplitude and the rising frequency (the rising time Tpr) thereof greatly affect the flow velocity waveform of the main jet. While the drive voltage has risen to the maximum voltage and gradually drops thereafter, the drive voltage does not particularly affect the flow velocity waveform of the main jet. Therefore, it is considered that the depth of excision becomes deep and the volume of excision becomes significant so as to be proportional thereto by raising the rising frequency or increasing the voltage amplitude.

However, there is a case where the depth of excision and the volume of excision of the excision target actually achieved do not necessarily change so as to answer the increase/decrease of the voltage characteristic value. Therefore, it has become clear that there is a case where the user-friendliness thereof is deteriorated. For example, there may be a case where the depth of excision and the volume of excision do not increase as intended even when an operator increases the voltage amplitude twice, or the depth of excision and the volume of excision do not decrease as expected even when the voltage amplitude is decreased to ½. Therefore, there can be an occurrence of a situation where the depth of excision and the volume of excision desired by an operator are not achieved. This is a problem that a surgical operation time is unavoidably elongated.

There is a case where the excision speed is intended to be adjusted separately from the strength of the pulsed liquid jet. As a specification thereof, a method performed by an operator instructing the repetitive frequency of the drive voltage waveform can be considered. For example, a raised repetitive frequency denotes that the number of times of ejection of the pulsed liquid jet per unit time is increased, leading to a change in the depth of excision and the volume of excision achieved at the final stage.

However, even though the repetitive frequency is changed based on the fact that the drive voltage waveform changes when the repetitive frequency is changed, the depth of excision and the volume of excision per unit time do not change in proportion thereto, thereby leading to a case where the user-friendliness is unfavorable for an operator. Specifically, for example, it is possible to consider a method of changing the repetitive frequency by simply increasing and reducing the drive voltage waveform in its entirety in the time axis direction. However, the method causes a fluctuation of the rising frequency which significantly affects the flow velocity waveform of the main jet so that the strength of the pulsed liquid jet changes as described above. Therefore, it is not possible to obtain the intended excision speed which is proportion to the repetitive frequency.

Therefore, while paying attention to the flow velocity waveform of the main jet, correlationship of the depth of excision and the volume of excision with some parameters which are determined by the flow velocity waveform of the main jet is studied. It is because when a parameter having the high correlationship with respect to the depth of excision and the volume of excision is found, it is possible to control the piezoelectric element 43 at the optimum drive voltage waveform in order to achieve the depth of excision and the volume of excision in accordance with the feeling of an operation for an operator.

Therefore, first, a mass flux [kg/s], a momentum flux [N], and an energy flux [W] of the main jet passing through the liquid ejection opening 551 are studied based on the flow velocity waveform of the main jet v [m/s] in the liquid ejection opening 551. The mass flux is mass [kg/s] per unit time of a liquid passing through the liquid ejection opening 551. The momentum flux is momentum [N] per unit time of a liquid passing through the liquid ejection opening 551. The energy flux is energy [W] per unit time of a liquid passing through the liquid ejection opening 551. The energy indicates the kinetic energy and will be abbreviated to "the energy" hereinafter.

Since a liquid is released to a free space in the liquid ejection opening 551, it is possible to consider the pressure to be substantially "0". The velocity in a direction orthogonal to the direction of ejecting a liquid jet (the radial direction of the liquid ejection opening 551) can also be considered to be substantially "0". When it is assumed that there is no velocity distribution of the liquid in the radial direction of the liquid ejection opening 551, the mass flux Jm [kg/s], the momentum flux Jp [N], and the energy flux Je [W] of a liquid passing through the liquid ejection opening 551 can be obtained through the following Expressions (1), (2), and (3). The sign S [m²] represents the cross-sectional area of the nozzle, and the sign ρ [kg/m³] indicates the density of an operation fluid.

$$Jm = S \times \rho \times v \quad (1)$$

$$Jp = S \times \rho \times v^2 \quad (2)$$

$$Je = \tfrac{1}{2} \times \rho \times S \times v^3 \quad (3)$$

Figure 4A:
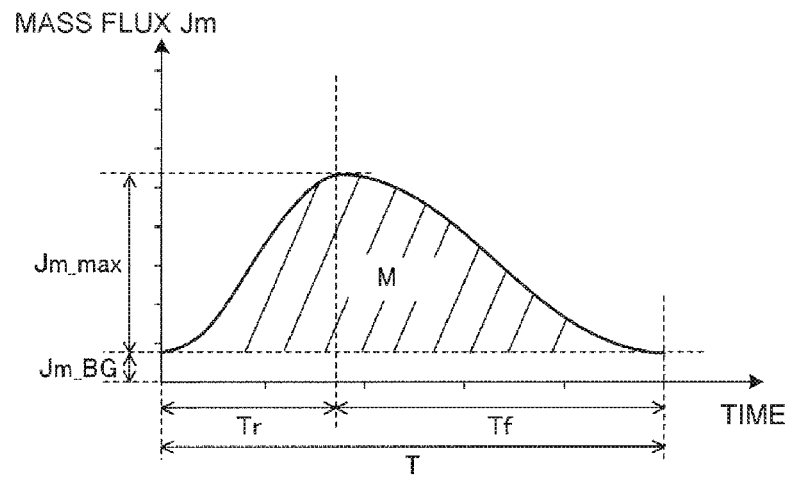
FIGS. 4A to 4C are diagrams illustrating a mass flux, a momentum flux, and an energy flux.
Figure 4B:
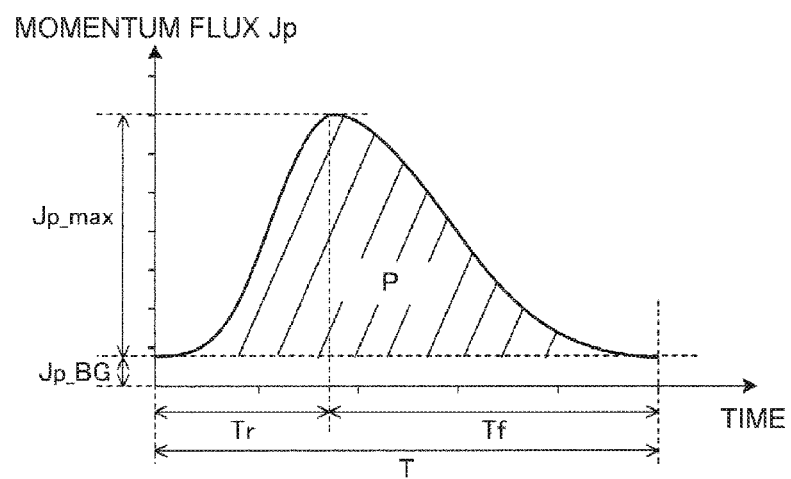
Figure 4C:
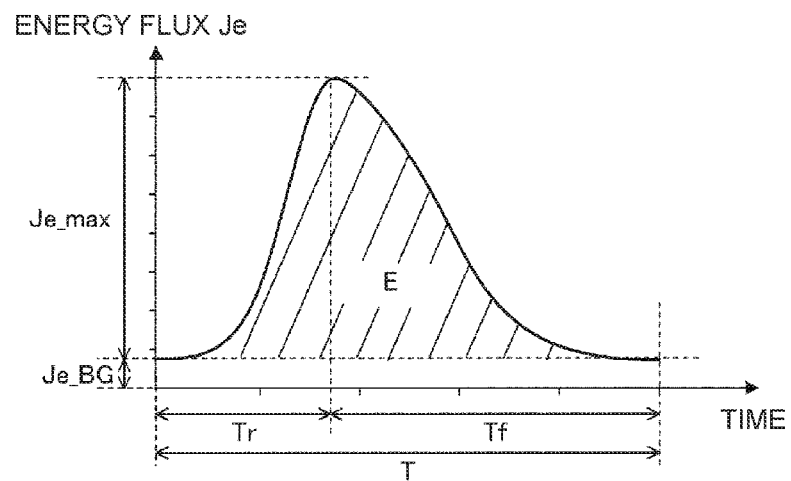

FIGS. 4A to 4C are diagrams illustrating a mass flux Jm (FIG. 4A), a momentum flux Jp (FIG. 4B), and an energy flux Je (FIG. 4C) obtained from the flow velocity waveform of the main jet illustrated in FIG. 3B. When each of the mass flux Jm, the momentum flux Jp, and the energy flux Je is integrated within a time (the duration) T from the rising to falling of the flow velocity waveform of the main jet, it is possible to obtain the mass, the momentum, and the energy of a liquid which is ejected as main jet from the liquid ejection opening 551.

It is considered that each of the values of the mass flux Jm, the momentum flux Jp, the energy flux Je, the mass, the momentum, and the energy calculated in the above-described manner can determine the depth of excision and the volume of excision resulted by the jet for one pulse. However, all of the above-referenced factors are physical quantities including the amount of the steady flow, and an important factor is a value from which the amount of contribution of the steady flow is subtracted.

Here, regarding the mass flux Jm in FIG. 4A, two parameters such as a maximum mass flux Jm_max [kg/s] obtained by subtracting a mass flux Jm_BG [kg/s] of the steady flow from the peak value (the maximum value) of the mass flux Jm, and flow-out mass M [kg] (illustrated in FIG. 4A in a hatched manner) obtained by excluding the amount of the steady flow from the mass of a liquid flowing out as the main jet from the liquid ejection opening 551 are defined. The flow-out mass M is expressed through the following Expression (4).

$$M = \int (Jm - Jm\_BG) dt \quad (4)$$

Regarding the momentum flux Jp in FIG. 4B, two parameters such as a maximum momentum flux Jp_max [N] obtained by subtracting a momentum flux Jp_BG [N] of the steady flow from the peak value (the maximum value) of the momentum flux Jp, and momentum P [Ns] (illustrated in FIG. 4B in a hatched manner) obtained by excluding the amount of the steady flow from the momentum of a liquid flowing out as the main jet from the liquid ejection opening 551 are defined. The momentum P is expressed through the following Expression (5).

$$P = \int (Jp - Jp\_BG) dt \quad (5)$$

Regarding the energy flux Je in FIG. 4C, two parameters such as a maximum energy flux Je_max [W] obtained by subtracting an energy flux Je_BG [W] of the steady flow from the peak value (the maximum value) of the energy flux Je, and an energy E [J] (illustrated in FIG. 4C in a hatched manner) obtained by excluding the amount of the steady flow from the energy of a liquid flowing out as the main jet from the liquid ejection opening 551 are defined. The energy E is expressed through the following Expression (6).

$$E = \int (Je - Je\_BG) dt \quad (6)$$

However, the interval of the integration in the above-referenced Expressions (4), (5), and (6) is the time (the duration) T from the rising to falling of the main jet in each of the flow velocity waveforms.

The degrees of correlationship of six parameters such as the maximum mass flux Jm_max, the flow-out mass M, the maximum momentum flux Jp_max, the momentum P, the maximum energy flux Je_max, and the energy E with respect to the depth of excision and the volume of excision are studied by utilizing numerical simulations.

Here, the pulsed liquid jet is a fluid, and the excision target is a soft elastic body. Therefore, in order to perform the simulations of the breakdown behavior of the excision target resulted by the pulsed liquid jet, a suitable breakdown threshold value has to be set on the soft elastic body side, and then, so-called coupled interpretation (fluid-structure coupled interpretation (FSI)) between the fluid and the structure body (in this case, the soft elastic body) has to be performed. As a calculation method of the simulation, for example, it is possible to exemplify a method using the finite element method (FEM), a method using a particle method represented by smoothed particle hydrodynamics (SPH) and the like, a method in which the finite element method and the particle method are combined, and the like. Since there is no particular limitation on the method to be applied, detailed description will not be given. However, an optimum method is selected and the simulation is performed in consideration of the stability of the interpretation result, the calculation time, and the like.

When performing the simulation, setting is performed under the condition of the density of the fluid=1 [g/cm$^3$], the diameter of the liquid ejection opening 551=0.15 [mm], and the stand-off distance (a distance from the liquid ejection opening 551 to the surface of the excision target)=0.5 [mm]. It is assumed that the excision target is a soft elastic body having a flat surface, and a Mooney-Rivlin super elastic body having the density of =1 [g/cm$^3$] and the modulus of elasticity of approximately 9 [kPa] in the Young's modulus conversion (approximately 3 [kPa] in the shear elastic modulus conversion) is used as a physical model. The strain corresponding to deviation=0.7 is used for the breakdown threshold value.

Regarding the flow velocity waveform of the main jet, various flow velocity waveforms of the main jet are postulated. Three types of waveforms such as a sine wave, a triangular wave, and a rectangular wave in three types of variations in each of the amplitude (the maximum value of the flow velocity) within the range from 12 [m/s] to 76 [m/s] and the duration within the range from 63 [μs] to 200 [μs], 27 types in total are prepared. The flow velocity of the steady flow is set to 1 [m/s].

Figure 5A:
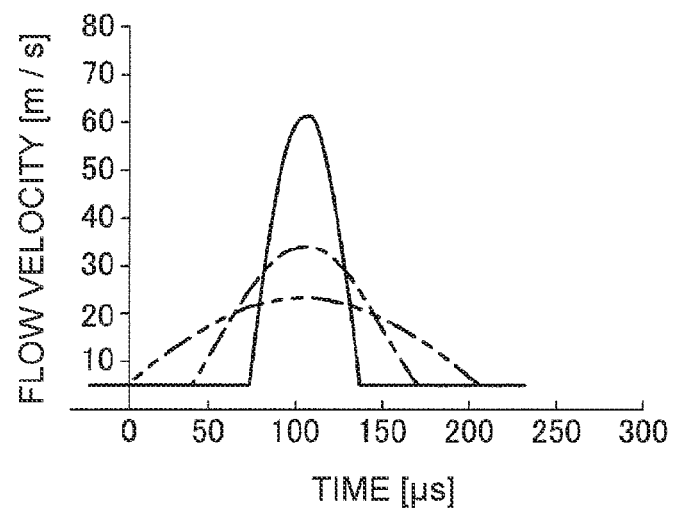
FIGS. 5A to 5C are diagrams illustrating flow velocity waveforms of a main jet used in simulations of excisional circumstances of an excision target.
Figure 5B:
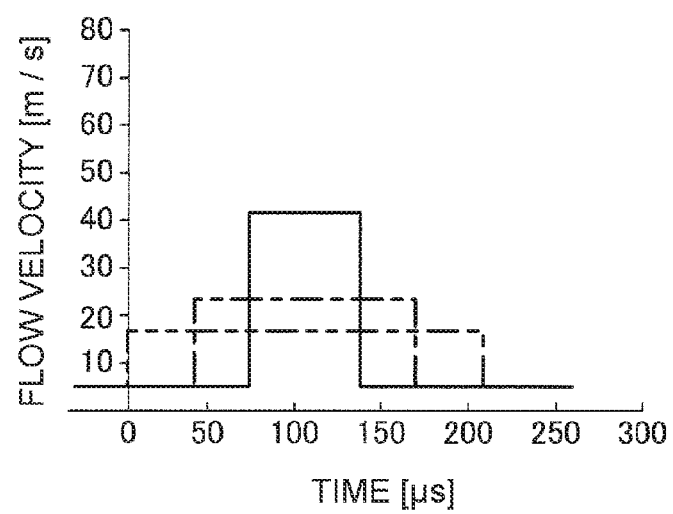
Figure 5C:
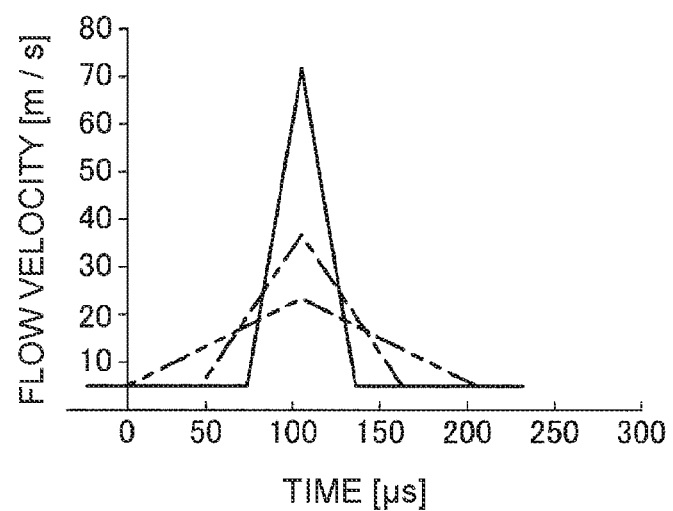

FIGS. 5A to 5C are diagrams illustrating a sine wave (FIG. 5A), the rectangular wave (FIG. 5B), and the triangular wave (FIG. 5C) which are applied as the flow velocity waveform of the main jet in the simulations. A waveform having the duration of 63 [μs] indicated by the solid line, a waveform having the duration of 125 [μs] indicated by the alternate long and short dash line, and a waveform having the duration of 200 [μs] indicated by the two-dot chain line are prepared for each of the waves. Then, a pulsed liquid jet is generated by applying the prepared waveform as the flow velocity waveform of the main jet, the simulation is performed regarding the breakdown behavior of the soft elastic body when the generated pulsed liquid jet is emitted to the soft elastic body, and the depth of excision and the volume of excision are thereby studied.

Figure 6A:
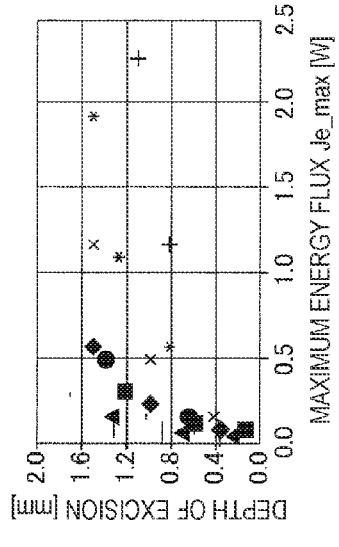
FIGS. 6A to 6F are diagrams illustrating simulation results (depth of excision).
Figure 6B:
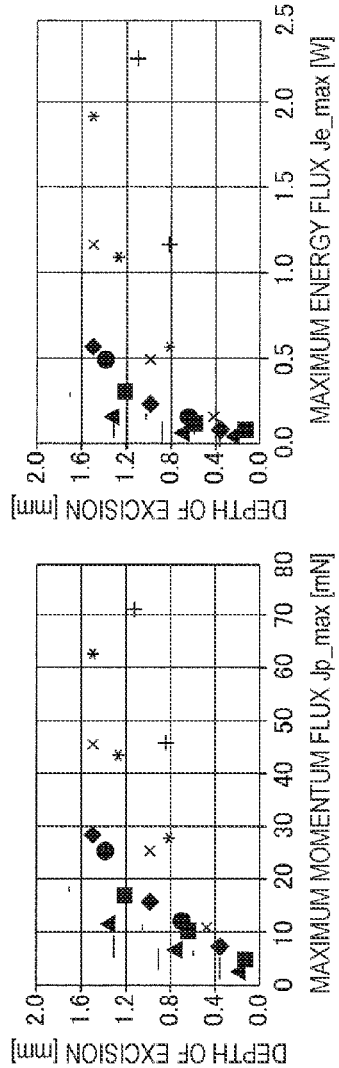
Figure 6C:
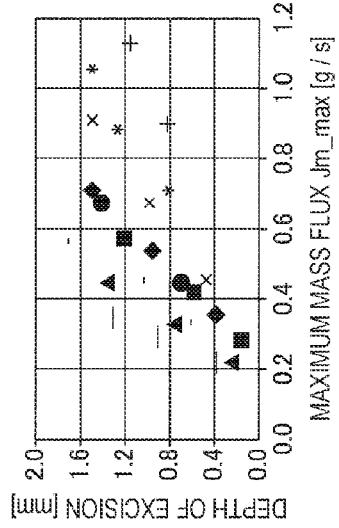
Figure 6D:
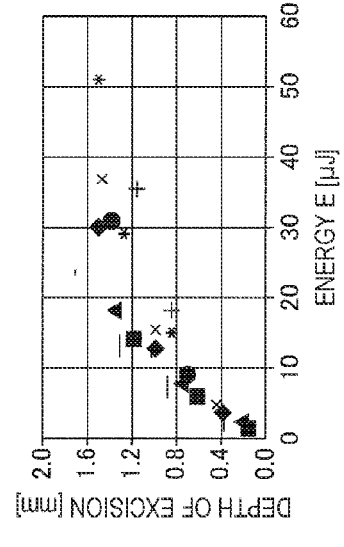
Figure 6E:
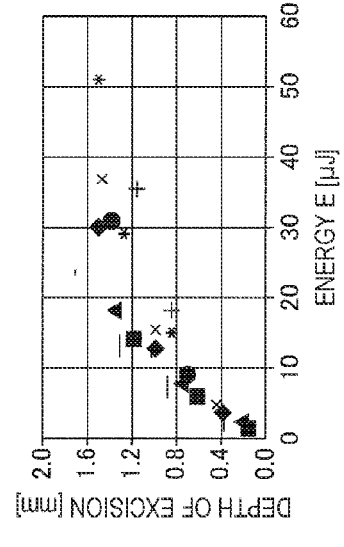
Figure 6F:
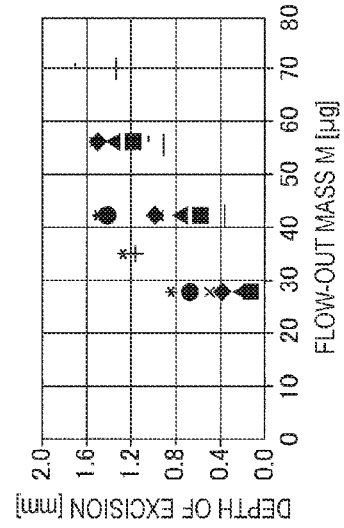

FIGS. 6A to 6F are diagrams in which simulation results are plotted while each thereof has the vertical axis as the depth of excision of the excision target, and the transverse axis as the maximum mass flux Jm_max (FIG. 6A), the flow-out mass M (FIG. 6B), the maximum momentum flux Jp_max (FIG. 6C), the momentum P (FIG. 6D), the maximum energy flux Je_max (FIG. 6E), and the energy E (FIG. 6F). In FIGS. 6A to 6F, the simulation result when the sine wave having the duration of 63 [μs] is applied as the flow velocity waveform of the main jet is plotted with the symbols "*", the simulation result when the sine wave having the duration of 125 [μs] is applied as the same is plotted with the symbols "♦", and the simulation result when the sine wave having the duration of 200 [μs] is applied as the same is plotted with the symbols "−". Moreover, the simulation result when the triangular wave having the duration of 63 [μs] is applied as the flow velocity waveform of the main jet is plotted with the symbols "+", the simulation result when the triangular wave having the duration of 125 [μs] is applied as the same is plotted with the symbols "×", and the simulation result when the triangular wave having the duration of 200 [μs] is applied as the same is plotted with the symbols "■". Furthermore, the simulation result when the rectangular wave having the duration of 63 [μs] is applied as the flow velocity waveform of the main jet is plotted with the signs "●", the simulation result when the rectangular wave having the duration of 125 [μs] is applied as the same is plotted with the black-colored triangle symbols, and the simulation result when the rectangular wave having the duration of 200 [μs] is applied as the same is plotted with the symbols "−".

As illustrated in FIGS. 6A, 6C, and 6E on the upper side, each of the relationships of three parameters such as the maximum mass flux Jm_max, the maximum momentum flux Jp_max, and the maximum energy flux Je_max with respect to the depth of excision is significantly scattered in accordance with the shape of the waveform applied as the flow velocity waveform of the main jet, and it is possible to know that the correlationship therebetween is low. Above all, since the mass flux is a value proportional to the flow velocity, it is implied that the depth of excision is not determined by only the maximum flow velocity of the main jet.

Next, according to each of the relationships of three parameters such as the flow-out mass M, the momentum P, and the energy E illustrated in FIGS. 6B, 6D, and 6F with respect to the depth of excision, the relationship between the flow-out mass M and the depth of excision is significantly scattered in accordance with the shape of the waveform applied as the flow velocity waveform of the main jet, and the correlationship therebetween is low. In contrast, in the relationships of the momentum P and the energy E with respect thereto, the scattering due to the shape of the applied waveform is small, and each of the plotted results is distributed on substantially the same curved line. The scattering of the momentum P is smaller when the momentum P and the energy E are compared. Therefore, it is possible to mention that the depth of excision is highly correlated to the momentum P and the energy E, and particularly, the depth of excision and the momentum P are in the favorable correlationship.

Here, the simulation is performed in a case where the diameter of the liquid ejection opening is set to 0.15 [mm] and the stand-off distance is set to 0.5 [mm]. However, the simulations are performed regarding other diameters of the liquid ejection opening and other stand-off distances, and it is checked that a qualitative tendency in which the depth of excision is highly correlated with the momentum P and the energy E does not remarkably change.

FIGS. 7A to 7F are diagrams in which simulation results are plotted while each thereof has the vertical axis as the volume of excision of the excision target, and the transverse axis as the maximum mass flux Jm_max (FIG. 7A), the flow-out mass M (FIG. 7B), the maximum momentum flux Jp_max (FIG. 7C), the momentum P (FIG. 7D), the maximum energy flux Je_max (FIG. 7E), and the energy E (FIG. 7F). The relationships of the waveforms applied as the flow velocity waveforms of the main jet with respect to the types of the plotted results are similar to those in FIGS. 6A to 6F.

As illustrated in FIGS. 7A, 7C, and 7E on the upper side, each of the relationships of three parameters such as the maximum mass flux Jm_max, the maximum momentum flux Jp_max, and the maximum energy flux Je_max with respect to the volume of excision is considered to be scattered in accordance with the shape of the waveform applied as the flow velocity waveform of the main jet not as much as that in the relationship with respect to the depth of excision. Therefore, it is considered that the correlationship therebetween is low.

Next, according to each of the relationships of three parameters such as the flow-out mass M, the momentum P, and the energy E illustrated in FIGS. 7B, 7D, and 7F with respect to the volume of excision, the relationship between the flow-out mass M and the volume of excision is significantly scattered in accordance with the shape of the waveform applied as the flow velocity waveform of the main jet similar to that of the depth of excision, and the correlationship therebetween is low. Meanwhile, in the relationships of the momentum P and the energy E with respect thereto, the scattering due to the shape of the applied waveform is small similar to that of the depth of excision, and each of the plotted results is distributed on substantially the same straight line. The scattering of the energy E is smaller compared to the momentum P. Therefore, it is possible to mention that the volume of excision is highly correlated to the momentum P and the energy E, and particularly, the volume of excision and the energy E are in the favorable correlationship.

Here, the simulation is performed in a case where the diameter of the liquid ejection opening is set to 0.15 [mm] and the stand-off distance is set to 0.5 [mm]. However, the simulations are performed regarding other diameters of the liquid ejection opening and other stand-off distances, and it is checked that a qualitative tendency in which the volume of excision is highly correlated with the momentum P and the energy E does not remarkably change.

Based on the studied results described above, in the embodiment, attention will be paid to the momentum P. Then, a simulation is performed in advance regarding the representative waveform as the drive voltage waveform to be actually applied to the piezoelectric element 43, thereby acquiring the correspondence relationships of the momentum P with respect to the rising frequency, the voltage amplitude, and the repetitive frequency.

Therefore, first, a control parameter is variably set, and the flow velocity waveform of the main jet is obtained through the simulation. For example, the simulation can be easily performed by utilizing a numerical simulation performed by using the equivalent circuit method based on a model in which the channel system of the liquid ejection device is replaced with the fluid (channel) resistance, the fluid inertance, the fluid compliance, and the like. Otherwise, when it is desired to obtain higher accuracy, a fluid simulation using the finite element method (FEM), the finite volume method (FVM), or the like may be utilized.

Figure 8A:
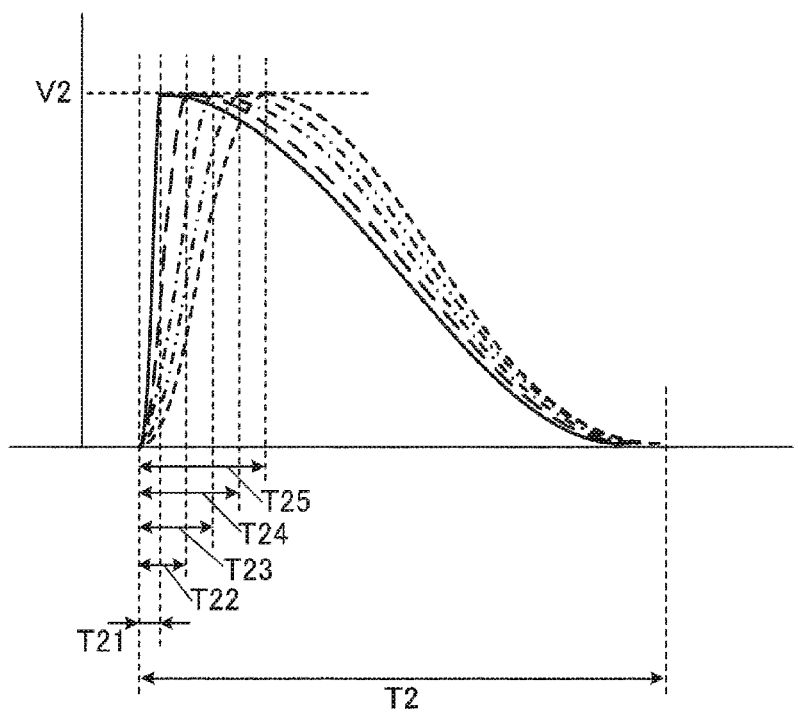
FIGS. 8A and 8B are diagrams illustrating simulation results of flow velocity waveforms of the main jet when drive voltage waveforms respectively having rising frequencies different from each other are applied.

Firstly, the voltage amplitude and the repetitive frequency are fixed, and the flow velocity waveform of the main jet is obtained through the simulation by applying the drive voltage waveform of which the rising frequency is changed in stages. FIG. 8A is a diagram illustrating an example of an applied drive voltage waveform. In each of the drive voltage waveforms, V2 represents the voltage amplitude, T2 represents the repetitive cycle Tp, and the rising time Tpr is elongated in stages from T21 to T25 (the rising frequency is lowered in stages).

Figure 8B:
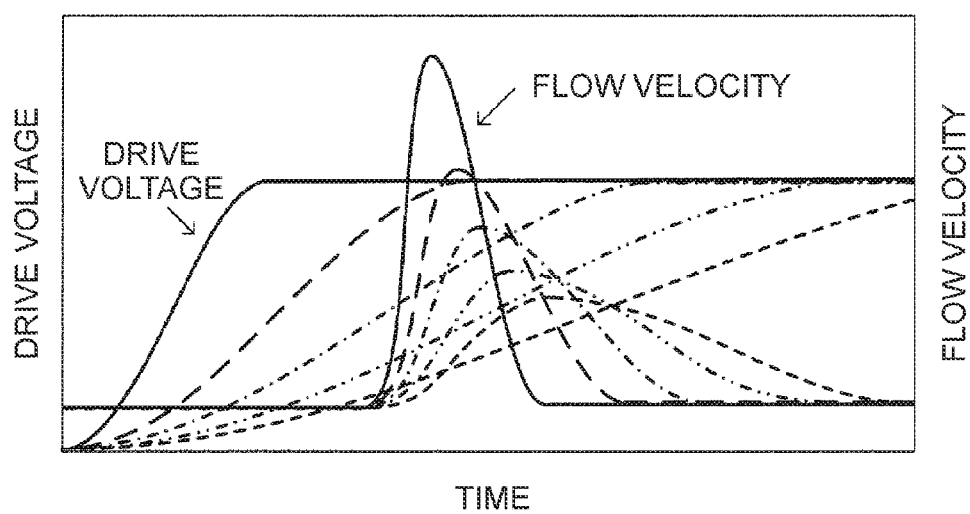

FIG. 8B is a diagram illustrating the simulation results of the flow velocity waveforms of the main jet when each of the drive voltage waveforms illustrated in FIG. 8A having the rising frequencies different from each other is applied. As illustrated in FIG. 8B, when the rising frequency is lowered (elongated as for the rising time Tpr), the duration for the rising of the flow velocity waveform of the main jet is elongated with no change in the start timing of the rising, and thus, the amplitude of the flow velocity (the maximum value of the flow velocity) also becomes small.

Figure 9A:
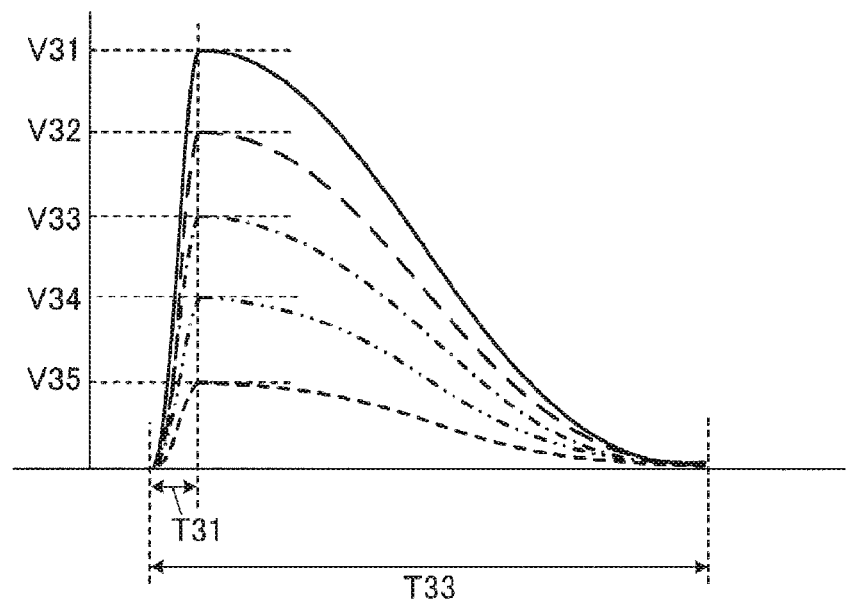
FIGS. 9A and 9B are diagrams illustrating simulation results of flow velocity waveforms of the main jet when drive voltage waveforms respectively having voltage amplitudes different from each other are applied.

Secondly, the rising frequency and the repetitive frequency are fixed, and the flow velocity waveform of the main jet is obtained through the simulation by applying the drive voltage waveform of which the voltage amplitude is changed in stages. FIG. 9A is a diagram illustrating an example of an applied drive voltage waveform. In each of the drive voltage waveforms, T31 represents the rising time Tpr, T33 represents the repetitive cycle Tp, and the voltage amplitude is reduced in stages from V31 to V35.

Figure 9B:
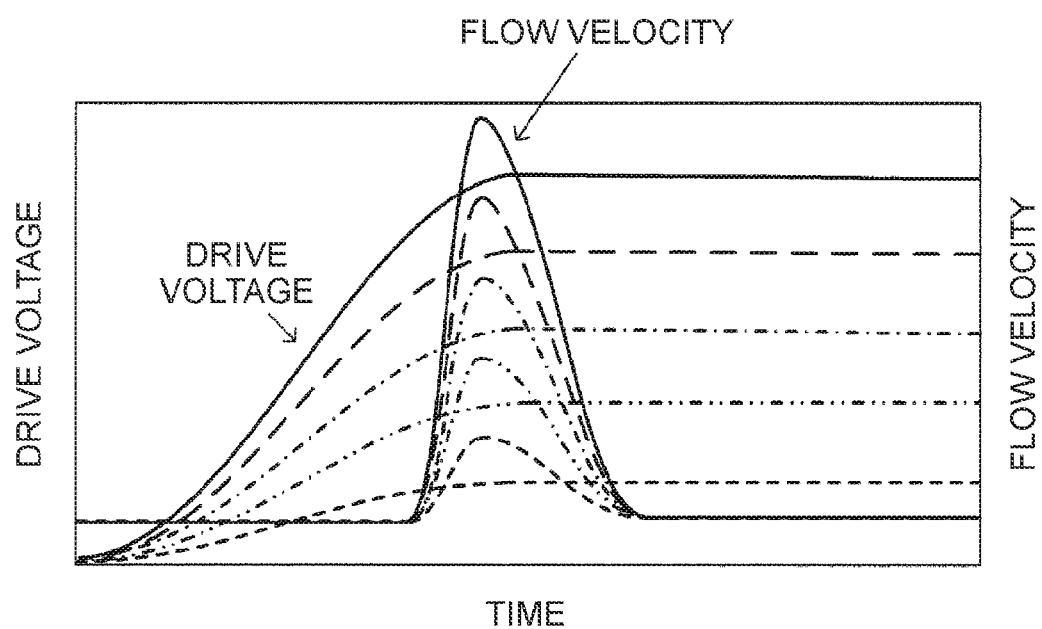

FIG. 9B is a diagram illustrating the simulation results of the flow velocity waveforms of the main jet when the drive voltage waveforms illustrated in FIG. 9A having the voltage amplitudes different from each other is applied. As illustrated in FIG. 9B, when the voltage amplitude is reduced, the amplitude of the flow velocity (the maximum value of the flow velocity) becomes small while the duration for the rising of the flow velocity waveform of the main jet is maintained being different from the case where the rising frequency is lowered.

Figure 10A:
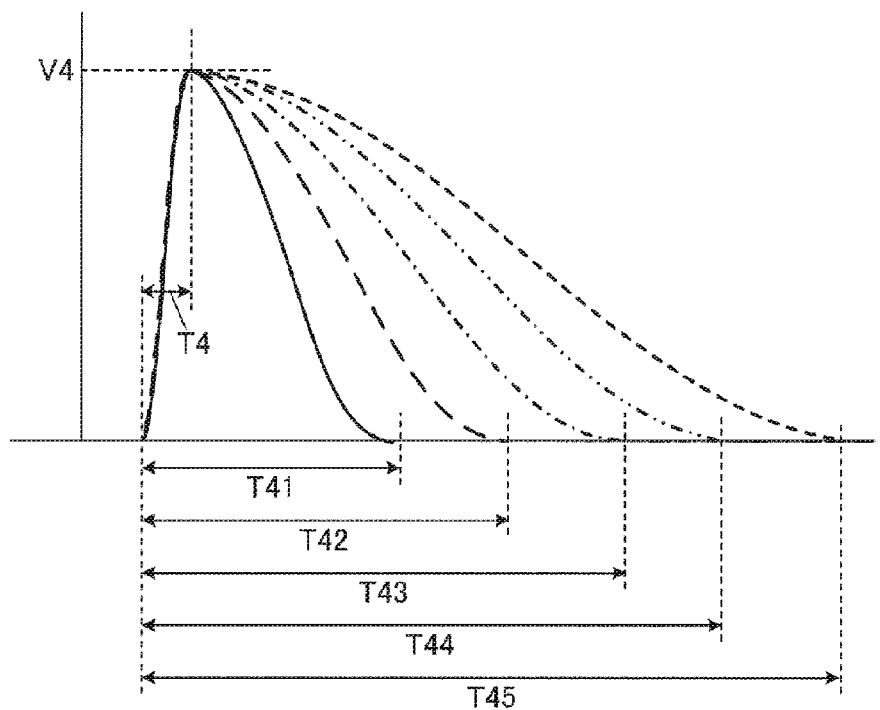
FIGS. 10A and 10B are diagrams illustrating simulation results of flow velocity waveforms of the main jet when drive voltage waveforms respectively having repetitive frequencies different from each other are applied.

Thirdly, the rising frequency and the voltage amplitude are fixed, and the flow velocity waveform of the main jet is obtained through the simulation by applying the drive voltage waveform of which the repetitive frequency is changed in stages. FIG. 10A is a diagram illustrating an example of an applied drive voltage waveform. In each of the drive voltage waveforms, T4 represents the rising time Tpr, V4 represents the voltage amplitude, and the repetitive cycle Tp is elongated in stages from T41 to T45 (the repetitive frequency is lowered in stages) by widening the shape of falling in the time axis direction after the drive voltage has risen to the maximum voltage.

Figure 10B:
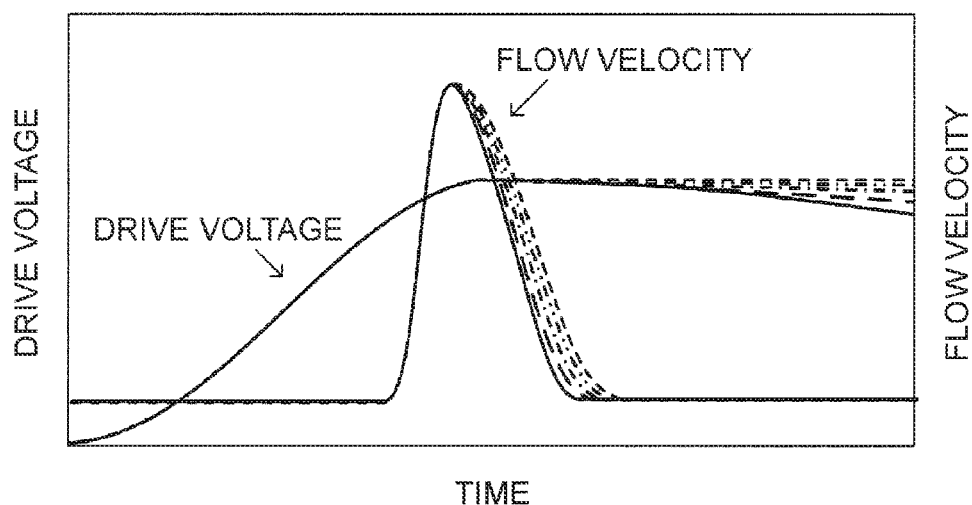

FIG. 10B is a diagram illustrating the simulation result of the flow velocity waveform of the main jet when the drive voltage waveforms illustrated in FIG. 10A having the repetitive frequencies different from each other is applied. As illustrated in FIG. 10B, when the repetitive frequency is lowered (elongated as for the repetitive cycle Tp), the duration of the flow velocity waveform of the main jet is elongated even though the degree thereof is smaller compared to the case where the rising frequency is lowered. The amplitude of the flow velocity (the maximum value of the flow velocity) remains maintained.

Subsequently, the momentum P is obtained for each of the acquired flow velocity waveforms of the main jet. In detail, the simulation of a case where the voltage amplitude is fixed for each of the repetitive frequencies as described with reference to FIGS. 8A and 8B and the rising frequencies are changed while changing the repetitive frequency as described with reference to FIGS. 10A and 10B, and the simulation of a case where the rising frequency is fixed and the voltage amplitude is changed as described with reference to FIGS. 9A and 9B are performed. Then, the momentum P of the flow velocity waveform of the main jet acquired in each simulation is obtained.

Figure 11:
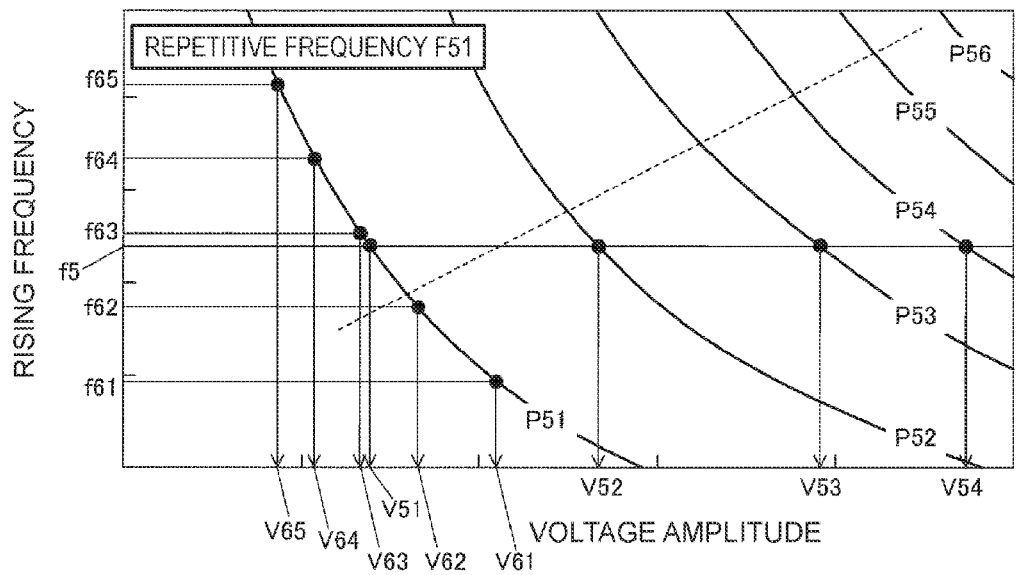
FIG. 11 is a diagram illustrating a correspondence relationship among momentum, the rising frequency, and the voltage amplitude at a predetermined repetitive frequency.

FIG. 11 is a diagram illustrating the correspondence relationship among the momentum P, the rising frequency, and the voltage amplitude acquired through a predetermined repetitive frequency (for example, marked with "F51"). FIG. 11 is obtained by drawing a contour line related to the momentum P in the coordinate space where the vertical axis indicates the rising frequency and the transverse axis indicates the voltage amplitude. The momentums P51, P52, and so forth of each of the contour lines are low on the lower left side in FIG. 11 and become greater toward the upper right side by a predetermined amount. When the momentum P acquired through a different repetitive frequency is plotted similarly in the coordinate space and another contour line is drawn (not illustrated), it is possible to acquire a contour diagram in accordance with the correspondence relationship among the momentum P, the rising frequency, and the voltage amplitude at the repetitive frequency thereof.

Here, a noteworthy factor is that the momentum P does not linearly change with respect to the parameter in each coordinate axis direction. For example, a case where the drive voltage waveform of the piezoelectric element 43 is controlled by causing the rising frequency to be fixed (for example, f5) and causing the voltage amplitude to be variable in the correspondence relationship among the momentum P, the rising frequency, and the voltage amplitude illustrated in FIG. 11 is considered. When the amount of change of the momentum P is intended to be regular, the section between the momentums P51 and P52 needs a change of the voltage amplitude in the section between the voltage amplitudes V51 and V52, and the section between the momentums P52 and P53 needs a change of the voltage amplitude in the section between the voltage amplitudes V52 and V53. However, the voltage amplitude interval between the voltage amplitudes V51 and V52, and the voltage amplitude interval between the voltage amplitudes V52 and V53 are different from each other. The phenomenon appears remarkably as the momentum P becomes greater. Therefore, since the momentum P does not change as expected when an operation in which the rising frequency is fixed and the voltage amplitude is changed by a regular amount is performed, there can be an occurrence of a situation where the depth of excision and the volume of excision do not change in accordance with the intention and the feeling of an operator. The similar situation occurs in a case of an operation in which the voltage amplitude is fixed and the rising frequency is changed by a regular amount.

Moreover, in the embodiment, since a plurality types of ejection tube sections 50 are provided so as to be attachable/detachable with respect to the main body section 40 in the liquid ejection device 30, and there is a case where the above-described correspondence relationship among the momentum P, the rising frequency, and the voltage amplitude varies in accordance with the ejection tube section type of the ejection tube section 50 mounted in the main body section 40, these factors need to be considered.

Therefore, in the embodiment, as operations performed by an operator during a surgical operation, at least an increasing/decreasing operation of the momentum P and an increasing/decreasing operation of the repetitive frequency are received. In addition, the contour diagram is obtained while changing the repetitive frequency in advance in the above-described manner with respect to each of the ejection tube section types of the ejection tube section 50 which can be mounted in the main body section 40, and the correspondence relationship among the momentum P, the rising frequency, and the voltage amplitude for each repetitive frequency is obtained and is arranged in the table. Then, at the time of a surgical operation, the correspondence relationship which is determined regarding the ejection tube section type of the ejection tube section 50 mounted in the main body section 40 is subjected to being a reference as the fitted correspondence relationship. In other words, during a surgical operation, the rising frequency and the voltage amplitude corresponding to the momentum P which is instructed based on the fitted correspondence relationship related to the instructed repetitive frequency are specified in accordance with the increasing/decreasing operation of the momentum P and the increasing/decreasing operation of the repetitive frequency performed by an operator, thereby controlling the drive of the piezoelectric element 43.

Exemplary Embodiment 1

Figure 12:
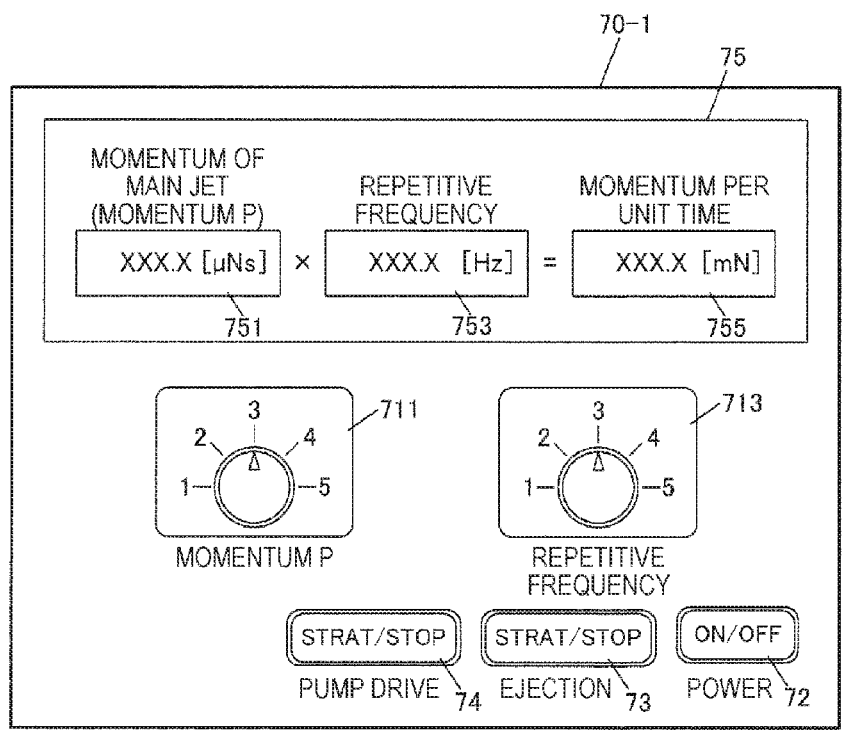
FIG. 12 is a diagram illustrating an operation panel of a liquid ejection control device in Exemplary Embodiment 1.

First, description will be given regarding Exemplary Embodiment 1. FIG. 12 is a diagram illustrating an operation panel 70-1 included in a liquid ejection control device 60-1 in Exemplary Embodiment 1. As illustrated in FIG. 12, a momentum dial 711 as a first operation unit, a repetitive frequency dial 713 as a second operation unit, a power button 72, an ejection button 73, a pump drive button 74, and a liquid crystal monitor 75 are arranged in the operation panel 70-1.

The momentum dial 711 is used for inputting an instruction value of the momentum P (a momentum instruction value) which is a first instruction value. For example, dial positions in five stages having graduated scales "1" to "5" are configured to be able to be selected. An operator performs the increasing/decreasing operation of the momentum P in five stages by switching the dial position of the momentum dial 711. For example, the momentum instruction values are allocated respectively for the dial positions in advance so as to be increased by a regular amount in proportion to the numerical value of the corresponding graduated scale. The number of stages for the dial positions is not limited to five stages. The dial positions may be appropriately set to have three stages such as "large", "medium", and "small", or to be adjustable with no stage.

The repetitive frequency dial 713 is used for inputting an instruction value of the repetitive frequency (a repetitive frequency instruction value) which is a second instruction value. Similar to the momentum dial 711, for example, dial positions in five stages of "1" to "5" are configured to be able to be selected. The repetitive frequency dial 713 may be configured to include an activation switch for switching between validness/invalidness of an operation with respect to the repetitive frequency dial 713 on the assumption that an operator mainly performs the increasing/decreasing operation of the momentum P. The operator switches the dial position of the repetitive frequency dial 713, thereby performing the increasing/decreasing operation in five stages with respect to the repetitive frequency of the drive voltage waveform (for example, several ten [Hz] to several hundred [Hz]) which is repetitively applied to the piezoelectric element 43. For example, the repetitive frequency instruction values are allocated respectively for the dial positions in advance so as to be increased by a regular amount in proportion to the numerical value of the corresponding graduated scale. The number of stages for the dial positions is not limited to five stages. The number of stages may be appropriately set. The number of stages may be different from that of the momentum dial 711.

In this manner, in Exemplary Embodiment 1, there are two operations such as the increasing/decreasing operation of the momentum P performed by using the momentum dial 711, and the increasing/decreasing operation of the repetitive frequency performed by using the repetitive frequency dial 713, which are performed by an operator during a surgical operation. The rising frequency is fixed, and the correspondence relationship between the momentum P and the voltage amplitude at a predetermined rising frequency is arranged for each of the repetitive frequencies in a table in advance. For example, when the rising frequency is set to f5 illustrated in FIG. 11, the voltage amplitudes V51, V52, and so forth on the intersection points with respect to each of the contour lines are caused to associate with the corresponding momentum P51, P52, and so forth on the contour line, thereby preparing the data table regarding the repetitive frequency F51 while having the rising frequency of f5. Regarding other repetitive frequencies, the data table is prepared for each thereof in a similar manner. In more detail, the data table is prepared for each of the ejection tube section types of the ejection tube section 50 which can be mounted in the main body section 40.

Here, the data table is prepared while the rising frequency is fixed. In contrast, for example, a reference line may be set within the coordinate space illustrated in FIG. 11, and the rising frequency and the voltage amplitude on each intersection point in which the reference line intersects each contour line of the momentum P may be acquired so as to be arranged in the table. For example, when the straight line indicated by the dotted line in FIG. 11 is set as the reference line, the rising frequencies and the voltage amplitudes on the intersection points with respect to each of the contour lines may associate with the corresponding momentums P51, P52, and so forth on the contour line, thereby preparing the data table. The reference line indicated by the dotted line in FIG. 11 does not have to be a straight line, for example, the reference line may be a curved line.

The momentums P51, P52, and so forth of the contour lines are allocated respectively for the dial positions 1, 2, and so forth of the momentum dial 711 in an ascending order as the momentum instruction values. In this manner, it is possible to cause the amounts of change of the momentum P when the momentum dial 711 is moved by one graduated scale to be approximately the same as each other.

Meanwhile, the repetitive frequencies used for preparing the data table are allocated respectively for the dial positions 1, 2, and so forth of the repetitive frequency dial 713 in order from the low number as the repetitive frequency instruction value. For example, when the graduated scale of the repetitive frequency dial 713 is moved without moving the momentum dial 711, it is possible to adjust the excision speed without changing the momentum P.

The power button 72 is used for switching between ON/OFF of the power. The ejection button 73 is used for switching between a start of ejection and a stop of ejection of a pulsed liquid jet and provides a function similar to that of the ejection pedal 81 illustrated in FIG. 1. The pump drive button 74 is used for switching between a start of supplying and a stop of supplying a liquid from the liquid delivery pump device 20 to the liquid ejection device 30.

In the operation panel 70-1, the liquid crystal monitor 75 displays a display screen showing the momentum P, that is, a momentum [μNs] 751 of the main jet for one pulse, a repetitive frequency [Hz] 753, and momentum per unit time obtained by multiplying the aforementioned factors, that is, force [mN] 755. A current value for each of the values (hereinafter, collectively referred to as "the momentum information") is updated and displayed. Here, a value displayed for the momentum 751 of the main jet is a current value of the momentum instruction value, and a value displayed for the repetitive frequency 753 is the repetitive frequency instruction value. Through the display screen, an operator can work while grasping the current values such as the momentum P, the repetitive frequency, and the momentum (force) per unit time related to the pulsed liquid jet ejected from the liquid ejection opening 551 during a surgical operation.

The display screen does not need to display all three of the momentum P, the repetitive frequency, and the momentum per unit time during a surgical operation as illustrated in FIG. 12. It is acceptable as long as the display screen is configured to display at least one of the momentum P and the repetitive frequency. In addition to the momentum P, the repetitive frequency, and the like, at least one of a current rising frequency (or a rising time Tpr) and the voltage amplitude may be displayed, or both thereof may be displayed together. The display of each of the values is not limited to a case performed by displaying the numerical values as illustrated in FIG. 12. The display may be performed through the meter display or may be performed through the graph display showing changes of the momentum P, the repetitive frequency, and the like entailed after the increasing/decreasing operation from the start of ejection of a pulsed liquid jet.

Figure 13:
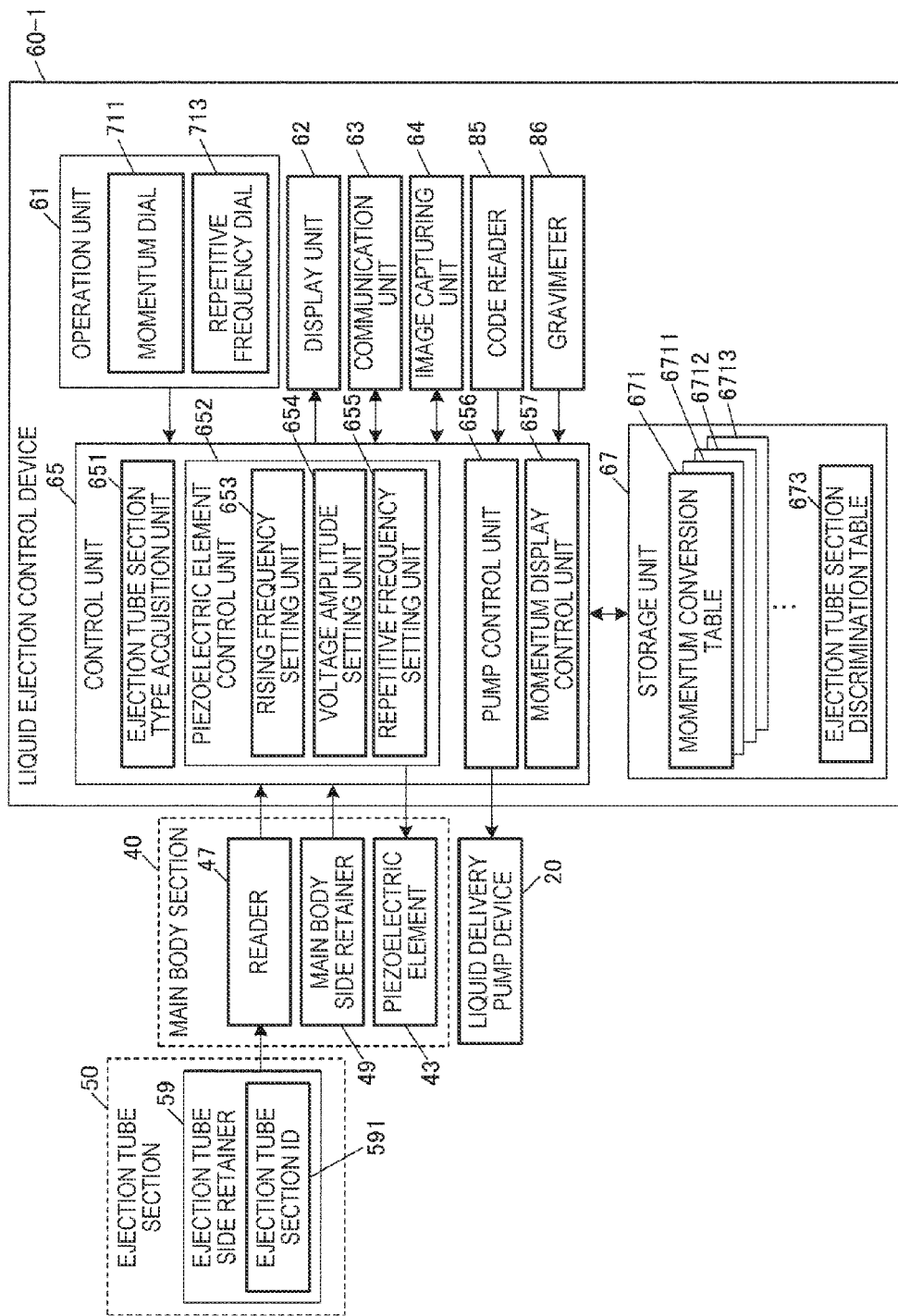
FIG. 13 is a block diagram illustrating an example of a functional configuration of the liquid ejection control device in Exemplary Embodiment 1.

FIG. 13 is a block diagram illustrating an example of the functional configuration of the liquid ejection control device in Exemplary Embodiment 1. As illustrated in FIG. 13, the liquid ejection control device 60-1 includes an operation unit 61, a display unit 62, a communication unit 63, an image capturing unit 64, the code reader 85, the gravimeter 86, a control unit 65, and a storage unit 67.

The operation unit 61 can be realized by various types of switches such as a button switch, a lever switch, a dial switch, and a pedal switch; and an input device such as a touch panel, a track pad, a keyboard, and a mouse. The operation unit 61 outputs an operational signal in accordance with an operational input to the control unit 65. The operation unit 61 includes the momentum dial 711 and the repetitive frequency dial 713. The operation unit 61 (not illustrated) also includes the ejection pedal 81 in FIG. 1; and the power button 72, the ejection button 73, and the pump drive button 74 on the operation panel 70-1 illustrated in FIG. 12.

The display unit 62 is realized by a display device such as a liquid crystal display (LCD), and an electroluminescence display (EL) display. The display unit 62 displays various types of screens such as the display screen illustrated in FIG.

12 based on the display signals input from the control unit 65. For example, the liquid crystal monitor 75 in FIG. 12 corresponds thereto.

The communication unit 63 is a communication device for transmitting and receiving information which is utilized inside the device, with respect to an external apparatus (for example, the server apparatus 100) while being under control performed by the control unit 65. The communication device 83 in FIG. 1 corresponds thereto. As a communication method of the communication unit 63, various types such as a cable connection form performed via a cable complying with a predetermined communication standard, a connection form performed via an intermediate device, that is, a so-called cradle which also serves as a charger, and wireless connection utilizing wireless communication can be applied.

The image capturing unit 64 is an image capturing device such as a camera and a scanner. The image capturing unit 64 corresponds to the image capturing device 84 in FIG. 1. The image capturing unit 64 is provided so as to acquire shape information of the ejection tube section 50. The image capturing unit 64 appropriately captures an image of the appearance of the ejection tube section 50 and outputs the generated image data to the control unit 65.

The code reader 85 is provided so as to read out an information code which is obtained by encoding an ejection tube section ID. The code reader 85 appropriately reads out and interprets the information code and outputs the ejection tube section ID to the control unit 65.

The gravimeter 86 is provided for acquiring weight information of the ejection tube section 50. The gravimeter 86 appropriately measures the weight of the ejection tube section 50 and outputs the measurement value to the control unit 65.

The control unit 65 is realized by a microprocessor such as a central processing unit (CPU) and a digital signal processor (DSP), a control device such as an application specific integrated circuit (ASIC), and an computation device. The control unit 65 collectively controls each unit in the liquid ejection system 1. The control unit 65 includes an ejection tube section type acquisition unit 651 serving as a type discrimination unit and a correspondence relationship acquisition unit, a piezoelectric element control unit 652, a pump control unit 656, and a momentum display control unit 657 serving as a display control unit. Each of the units configuring the control unit 65 may be configured to be hardware such as an exclusive module circuit.

The ejection tube section type acquisition unit 651 discriminates the ejection tube section type of the ejection tube section 50 mounted in the main body section 40 by acquiring an ejection tube section ID 591 which is read out from the ejection tube side retainer 59 by the reader 47. The ejection tube section type acquisition unit 651 acquires the fitted correspondence relationship by reading out an momentum conversion table of the acquired ejection tube section ID from the storage unit 67.

The piezoelectric element control unit 652 includes a rising frequency setting unit 653, a voltage amplitude setting unit 654, and a repetitive frequency setting unit 655. In accordance with the dial position of the momentum dial 711 and the dial position of the repetitive frequency dial 713, the rising frequency setting unit 653 sets the rising frequency of the drive voltage waveform, the voltage amplitude setting unit 654 sets the voltage amplitude of the drive voltage waveform, and the repetitive frequency setting unit 655 sets the repetitive frequency of the drive voltage waveform.

The piezoelectric element control unit 652 sets the drive voltage waveform in accordance with the rising frequency, the voltage amplitude, and the repetitive frequency set by each of the units 653, 654, and 655. The piezoelectric element control unit 652 controls the drive signal of the set waveform to be applied to the piezoelectric element 43. In this case, the piezoelectric element control unit 652 as a rising shape setting unit variably sets the waveform shape of the falling portion (falling waveform) of the drive voltage waveform in a manner as illustrated in FIG. 10A so as to cause the repetitive frequency to be a frequency which is set as the repetitive frequency instruction value by the repetitive frequency setting unit 655.

The pump control unit 656 outputs a drive signal to the liquid delivery pump device 20, thereby driving the liquid delivery pump device 20. The momentum display control unit 657 controls the display unit 62 to display the momentum instruction value (that is, a current value of the momentum P) allocated for the dial position of the momentum dial 711 in the midst of selection, the repetitive frequency instruction value (that is, a current value of the repetitive frequency) allocated for the dial position of the repetitive frequency dial 713 in the midst of selection, and the momentum per unit time obtained by multiplying the aforementioned factors.

The storage unit 67 is realized by various types of IC memories such as a read only memory (ROM), a flash ROM, and a random access memory (RAM); and a storage medium such as a hard disk. The storage unit 67 appropriately includes a device for reading data thereof. A program for operating the liquid ejection system 1 and realizing various types of functions included in the liquid ejection system 1, data to be used during the execution of the program, and the like are stored in the storage unit 67 in advance or are temporarily stored every time processing is performed. The storage unit 67 includes the memory card 821 and the reader/writer 82 illustrated in FIG. 1.

The storage unit 67 also stores a plurality of momentum conversion tables 671, 6711, 6712, 6713, and so forth. The momentum conversion tables 671, 6711, 6712, 6713, and so forth are data tables in which the correspondence relationship among the momentum P, the rising frequency, and the voltage amplitude for each of the above-described repetitive frequencies is individually determined with reference to FIG. 11. Here, the correspondence relationship is related to each of the ejection tube section types of the ejection tube section 50 which can be mounted in the main body section 40. The momentum conversion tables 6711, 6712, 6713, and so forth are not exemplified herein. However, the momentum conversion tables 6711, 6712, 6713, and so forth are the momentum conversion tables determined for each type of the ejection tubes, and the form thereof is similar to that of the momentum conversion table 671.

FIG. 14 is a diagram illustrating an example of the data configuration of the momentum conversion table 671 in Exemplary Embodiment 1, and exemplifies the momentum conversion table 671 for the ejection tube section ID of "ID_001". As illustrated in FIG. 14, the momentum conversion table 671 is a data table in which the ejection tube section ID, the dial position (the graduated scale) of the repetitive frequency dial 713, the repetitive frequency instruction value allocated for the dial position, the dial position of the momentum dial 711, the momentum instruction value allocated for the dial position, the voltage amplitude, and the rising frequency are associated with each other. The correspondence relationship between the momentum P and the voltage amplitude at a predetermined rising frequency f_001 is set for each of the repetitive frequencies.

For example, when the ejection tube section ID read out from the ejection tube side retainer 59 by the reader 47 is "ID_001", the ejection tube section type acquisition unit 651 acquires the momentum conversion table 671 of FIG. 14 as the fitted correspondence relationship from the momentum conversion tables 671, 6711, 6712, 6713, and so forth which are determined for each of the ejection tube section types. Hereinafter, the momentum conversion table acquired as the fitted correspondence relationship is also referred to as "the fitted momentum conversion table". In this case, the rising frequency setting unit 653 sets the rising frequency to be fixed as f_001. The voltage amplitude setting unit 654 reads out the voltage amplitude corresponding to the combination of each of the dial positions of the momentum dial 711 and the repetitive frequency dial 713 in the midst of selection from the fitted momentum conversion table 671, thereby performing the setting. When any one of the momentum dial 711 and the repetitive frequency dial 713 is operated, the voltage amplitude setting unit 654 reads out the voltage amplitude corresponding to the combination of the dial positions of each of dials 711 and 713 from the fitted momentum conversion table 671, thereby updating the setting.

The repetitive frequency setting unit 655 reads out the repetitive frequency instruction value corresponding to the dial position of the repetitive frequency dial 713 in the midst of selection from the fitted momentum conversion table 671, thereby setting the repetitive frequency. When the repetitive frequency dial 713 is operated, the repetitive frequency setting unit 655 reads out the repetitive frequency instruction value of the selected dial position from the fitted momentum conversion table 671, thereby updating the setting of the repetitive frequency.

Figure 15:
FIG. 15 is a diagram illustrating an example of a data configuration of an ejection tube section discrimination table.
Figure 15:
Figure 15:
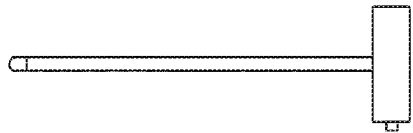
Figure 15:

Returning to FIG. 13, an ejection tube section discrimination table 673 is also appropriately stored in the storage unit 67. FIG. 15 is a diagram illustrating an example of the data configuration of the ejection tube section discrimination table 673. As illustrated in FIG. 15, the ejection tube section discrimination table 673 is a data table in which shape conditions and weight conditions are set while being associated with the ejection tube section ID. For example, the outer shape of the ejection tube section 50 of the corresponding ejection tube section ID is set for the shape condition, and the weight of the ejection tube section of the corresponding ejection tube section ID is set for the weight condition. Therefore, even though the ejection tube section ID (that is, the ejection tube section type) of the ejection tube section is unclear, when any one of or both the shape and the weight thereof are ascertained, it is possible to determine that which ejection tube section ID (that is, the ejection tube section type) the ejection tube section corresponds to by using the ejection tube section discrimination table 673. As described below, the ejection tube section type acquisition unit 651 may discriminate the ejection tube section type of the ejection tube section 50 mounted in the main body section 40 with reference to the ejection tube section discrimination table 673.

Flow of Processing

Figure 16:
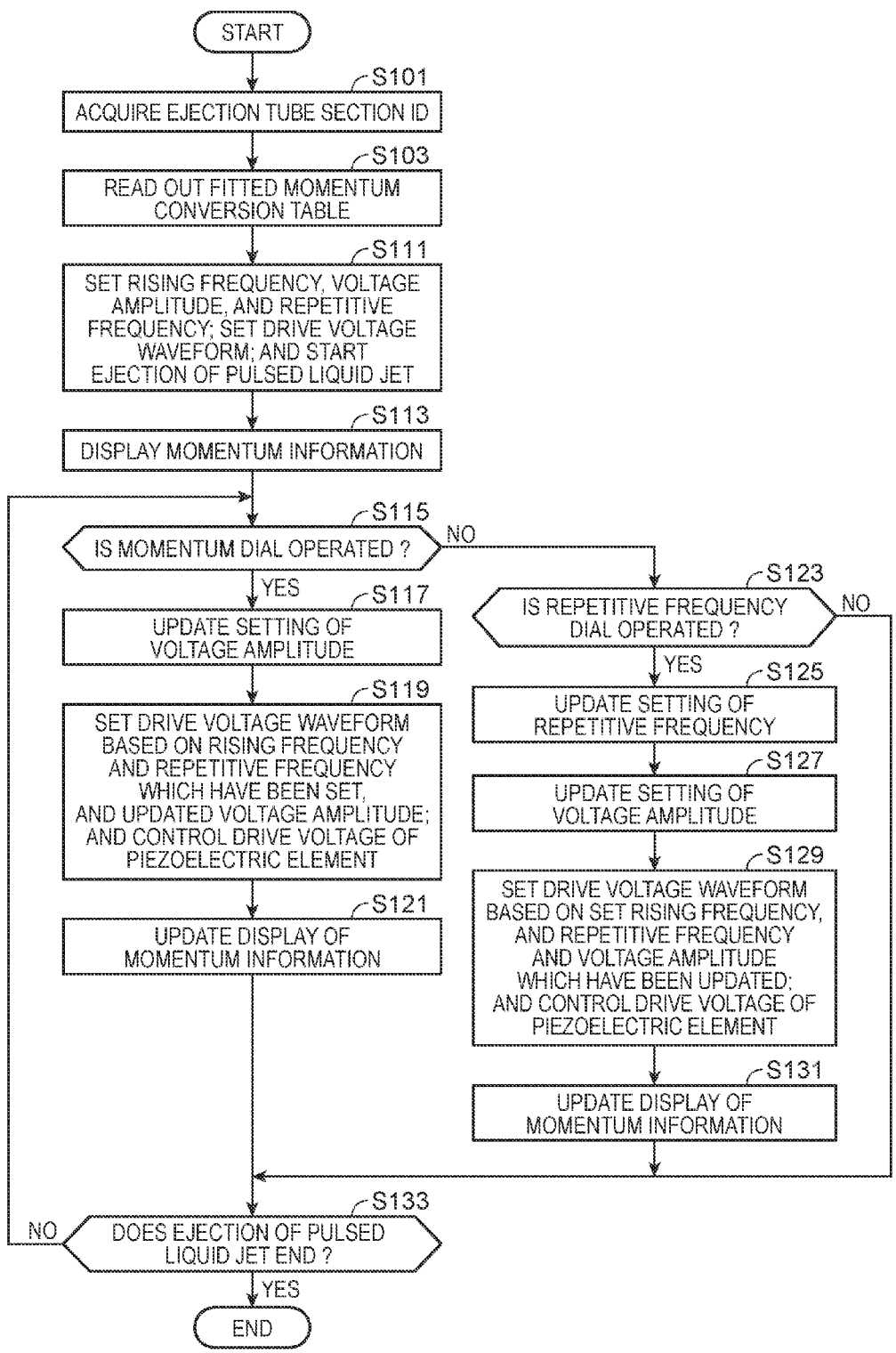
FIG. 16 is a flow chart illustrating a flow of processing performed by a control unit at the time of ejection of a pulsed liquid jet in Exemplary Embodiment 1.

FIG. 16 is a flow chart illustrating a flow of processing performed by the control unit 65 at the time of ejection of a pulsed liquid jet. First, the ejection tube section type acquisition unit 651 controls reading-out of the ejection tube section ID 591 performed by the reader 47 and acquires the ejection tube section ID readout from the ejection tube side retainer 59 by the reader 47 (Step S101). Then, the ejection tube section type acquisition unit 651 reads out the fitted momentum conversion table of the ejection tube section ID acquired in Step S101 from the momentum conversion tables 671, 6711, 6712, 6713, and so forth for each of the ejection tube section types stored in the storage unit 67 (Step S103).

Thereafter, the pump control unit 656 drives the liquid delivery pump device 20 in accordance with the fitted momentum conversion table, and the piezoelectric element control unit 652 drives the piezoelectric element 43, thereby starting ejection of a pulsed liquid jet (Step S111). In this case, the rising frequency setting unit 653 reads out the rising frequency which is set as a fixed value in the fitted momentum conversion table, thereby performing setting. The voltage amplitude setting unit 654 acquires the dial positions of the momentum dial 711 and the repetitive frequency dial 713 in the midst of selection, thereby reading out the voltage amplitude corresponding to the combination from the fitted momentum conversion table, thereby performing setting. Moreover, the repetitive frequency setting unit 655 reads out the repetitive frequency instruction value allocated for the dial position of the repetitive frequency dial 713 in the midst of selection from the fitted momentum conversion table, thereby setting the repetitive frequency. Then, the piezoelectric element control unit 652 sets the drive voltage waveform in accordance with the rising frequency, the voltage amplitude, and the repetitive frequency and applies the drive signal of the set drive voltage waveform to the piezoelectric element 43.

The momentum display control unit 657 controls the display unit 62 to display the momentum information (Step S113). For example, the momentum display control unit 657 reads out the momentum instruction value allocated for the dial position of the momentum dial 711 from the fitted momentum conversion table, thereby calculating the momentum per unit time which is the product obtained by multiplying the repetitive frequency instruction value read out in Step S111. Then, the momentum display control unit 657 performs processing to cause the display unit 62 to display the display screen in which the momentum instruction value, the repetitive frequency instruction value, and the momentum per unit time are displayed as the momentum information. The momentum per unit time is not limited to the configuration in which calculation is performed when displaying of the momentum information is controlled. The momentum per unit time may be configured to be set in the momentum conversion table so as to be read out.

Thereafter, until it is determined to end ejection of a pulsed liquid jet by operating the ejection pedal 81 or the ejection button 73 (Step S133: NO), the control unit 65 monitors the operation of the momentum dial 711 in Step S115 and monitors the operation of the repetitive frequency dial 713 in Step S123.

Then, when the momentum dial 711 is operated (Step S115: YES), the voltage amplitude setting unit 654 reads out the voltage amplitude corresponding to the combination of the selected dial position and the dial position of the repetitive frequency dial 713 in the midst of selection from the fitted momentum conversion table, thereby updating the setting of the voltage amplitude (Step S117). Thereafter, the piezoelectric element control unit 652 sets the drive voltage waveform in accordance with the repetitive frequency, the rising frequency, and the voltage amplitude which have been set, and applies the drive signal of the set drive voltage waveform to the piezoelectric element 43 (Step S119).

The momentum display control unit 657 reads out the momentum instruction value allocated for the selected dial position from the fitted momentum conversion table, thereby controlling the update of the display of the display unit 62 (Step S121).

Meanwhile, when the repetitive frequency dial 713 is operated (Step S123: YES), the repetitive frequency setting unit 655 reads out the repetitive frequency instruction value allocated for the selected dial position from the fitted momentum conversion table, thereby updating the setting of the repetitive frequency (Step S125). Subsequently, the voltage amplitude setting unit 654 reads out the voltage amplitude corresponding to the combination of the selected dial position and the dial position of the momentum dial 711 in the midst of selection from the fitted momentum conversion table, thereby updating the setting of the voltage amplitude (Step S127). Thereafter, the piezoelectric element control unit 652 sets the drive voltage waveform in accordance with the repetitive frequency, the rising frequency, and the voltage amplitude which have been set, and applies the drive signal of the drive voltage waveform to the piezoelectric element 43 (Step S129).

The momentum display control unit 657 reads out the repetitive frequency allocated for the selected dial position from the fitted momentum conversion table, thereby controlling the update of the display of the display unit 62 (Step S131).

According to Exemplary Embodiment 1, in the liquid ejection device 30, the correspondence relationship (the momentum conversion tables 671, 6711, 6712, 6713, and so forth for each of the ejection tube section types) between the momentum P and the voltage amplitude at a predetermined rising frequency is determined in advance for each of the repetitive frequencies with respect to each of the ejection tube section types of the ejection tube section 50 which can be mounted in the main body section 40. Then, prior to a surgical operation, it is possible to discriminate the ejection tube section type of the ejection tube section 50 mounted in the main body section 40 and to acquire the fitted correspondence relationship fitting the discriminated ejection tube section type. Moreover, during the surgical operation, with reference to the fitted correspondence relationship, it is possible to set the optimum voltage amplitude optimal for achieving the depth of excision and the volume of excision in accordance with the intended feeling of the operation and to control the drive voltage waveform of the piezoelectric element 43. For example, since the momentum P changes by the amount corresponding to the graduated scale interval when the momentum dial 711 is moved by one graduated scale, it is possible to realize the depth of excision and the volume of excision answering the intention of a user or feeling of the operation, and thus, the user-friendliness thereof can be improved.

The repetitive frequency can be raised and lowered so as to cause the momentum P to meet the momentum instruction value. Therefore, for example, when only the graduated scale of the repetitive frequency dial 713 is moved without moving the graduated scale of the momentum dial 711, it is possible to adjust the excision speed as intended so as to be proportional to the repetitive frequency while the depth of excision and the volume of excision caused by the pulsed liquid jet for one pulse is regularly maintained. Thus, an improvement of the user-friendliness thereof can be achieved.

Exemplary Embodiment 2

Figure 17:
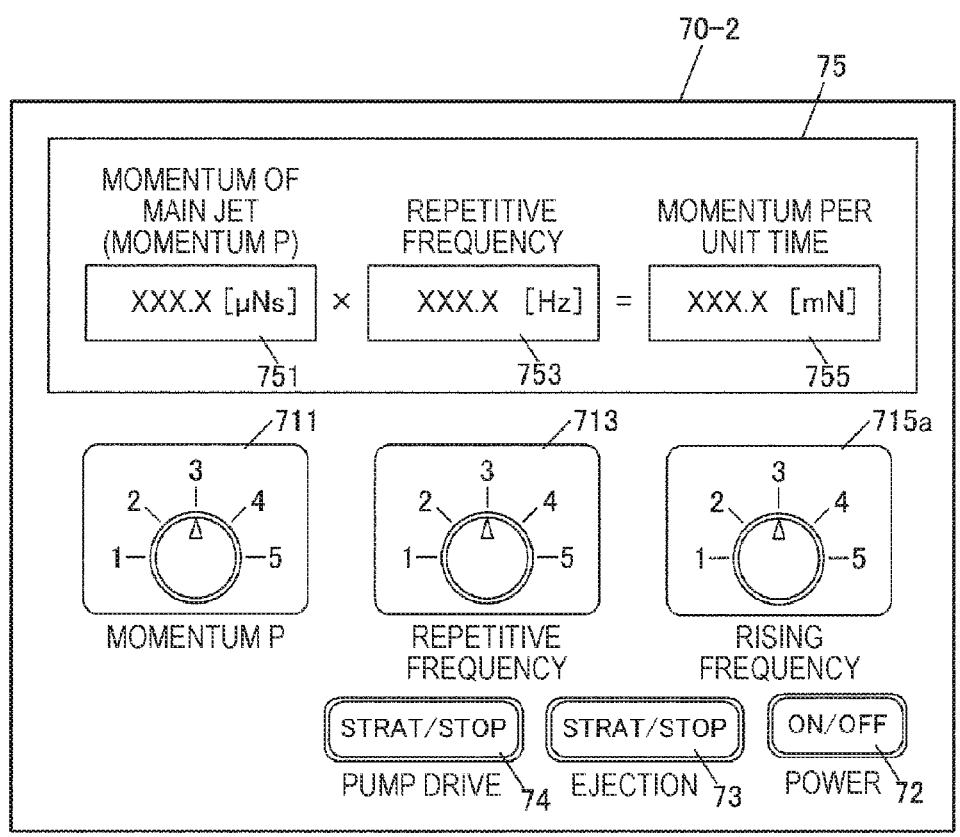
FIG. 17 is a diagram illustrating an operation panel of a liquid ejection control device in Exemplary Embodiment 2.

Next, description will be given regarding Exemplary Embodiment 2. The same reference numerals and signs will be applied to the portions similar to those in Exemplary Embodiment 1. FIG. 17 is a diagram illustrating an operation panel 70-2 included in a liquid ejection control device 60-2 in Exemplary Embodiment 2. As illustrated in FIG. 17, the momentum dial 711, the repetitive frequency dial 713, a rising frequency dial 715*a* as a third operation unit, the power button 72, the ejection button 73, the pump drive button 74, and the liquid crystal monitor 75 are arranged in the operation panel 70-2.

The rising frequency dial 715*a* is used for inputting an instruction value of the rising frequency (a rising frequency instruction value) as a third instruction value. For example, dial positions in five stages having graduated scales "1" to "5" are configured to be able to be selected. Similar to the repetitive frequency dial 713, the rising frequency dial 715*a* may also be configured to include the activation switch. An operator performs the increasing/decreasing operation of the rising frequency in five stages by switching the dial position of the rising frequency dial 715*a*. The rising frequency instruction value is allocated for each of the dial positions in advance so as to be increased by a regular amount in proportion to the numerical value of the corresponding graduated scale. The number of stages for the dial positions is not limited to five stages. The number of stages may be appropriately set. The number of stages may be different from those of the momentum dial 711 and the repetitive frequency dial 713.

In this manner, in Exemplary Embodiment 2, there are three operations such as the increasing/decreasing operation of the momentum P performed by using the momentum dial 711, the increasing/decreasing operation of the repetitive frequency performed by using the repetitive frequency dial 713, and the increasing/decreasing operation of the rising frequency performed by using the rising frequency dial 715*a*, which are performed by an operator during a surgical operation. The correspondence relationship among the momentum P, the rising frequency, and the voltage amplitude is arranged for each of the repetitive frequencies in a table. While paying attention to an momentum P51 illustrated in FIG. 11, for example, a data table in which rising frequencies f61, f62, and so forth having the frequency interval at equal intervals are associated with voltage amplitudes V61, V62, and so forth on the intersection points with respect to the contour line thereof is prepared. In more detail, the data table is prepared for each of the ejection tube section types of the ejection tube section 50 which can be mounted in the main body section 40. The rising frequencies f61, f62, and so forth are allocated respectively for the dial positions 1, 2, and so forth of the rising frequency dial 715*a* in order as the rising frequency instruction value.

Figure 18:
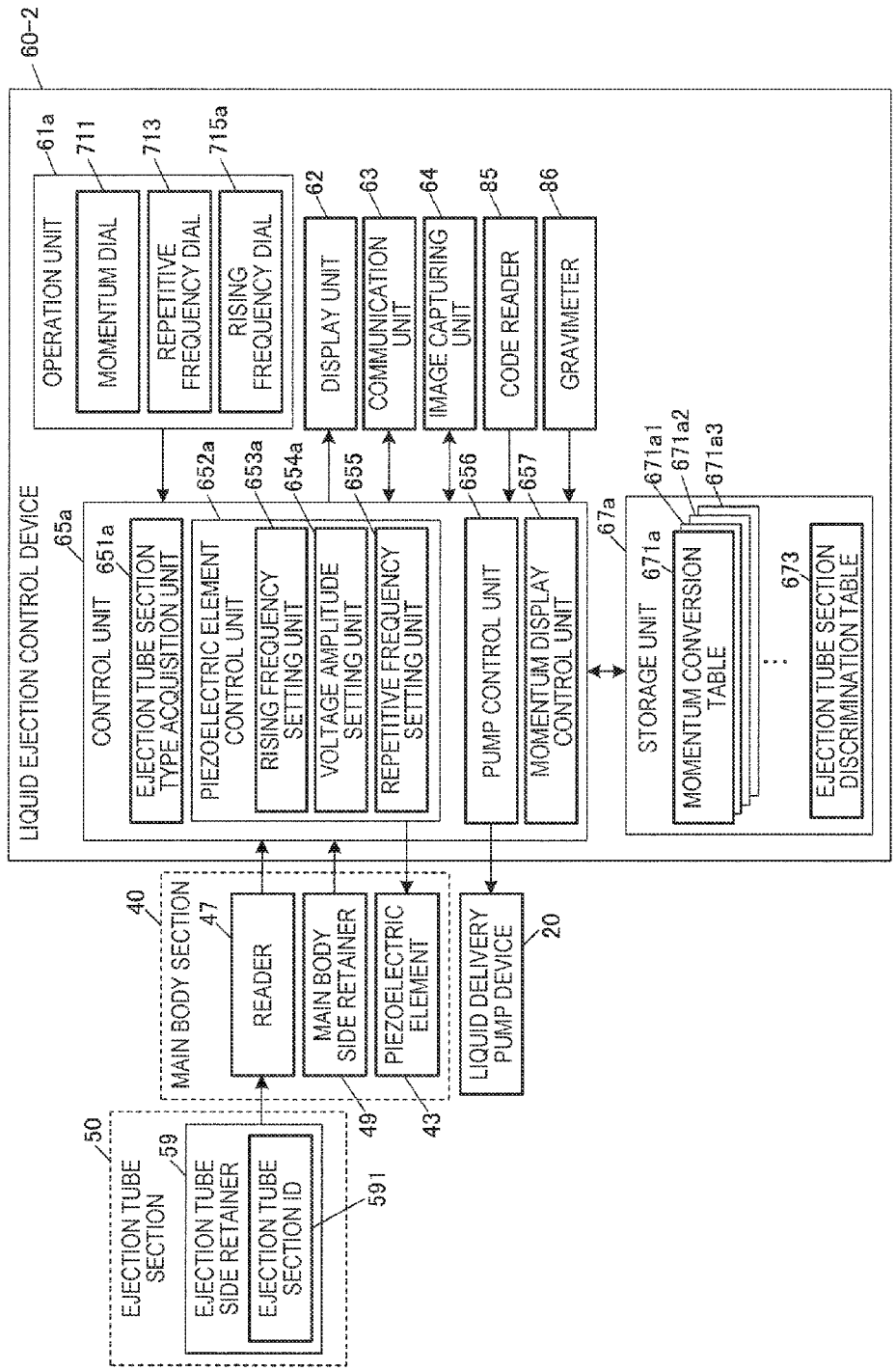
FIG. 18 is a block diagram illustrating an example of a functional configuration of the liquid ejection control device in Exemplary Embodiment 2.

FIG. 18 is a block diagram illustrating an example of the functional configuration of the liquid ejection control device in Exemplary Embodiment 2. As illustrated in FIG. 18, the liquid ejection control device 60-2 includes an operation unit 61*a*, the display unit 62, a control unit 65*a*, and a storage unit 67*a*.

The operation unit 61*a* includes the momentum dial 711, the repetitive frequency dial 713, and the rising frequency dial 715*a*.

The control unit 65*a* includes an ejection tube section type acquisition unit 651*a*, a piezoelectric element control unit 652*a*, the pump control unit 656, and the momentum display control unit 657. The piezoelectric element control unit 652*a* includes a rising frequency setting unit 653*a*, a voltage amplitude setting unit 654*a*, and the repetitive frequency setting unit 655.

The storage unit 67a stores a plurality of momentum conversion tables 671a, 671a1, 671a2, 671a3, and so forth; and the ejection tube section discrimination table 673. Similar to Exemplary Embodiment 1, the momentum conversion tables 671a, 671a1, 671a2, 671a3, and so forth are data tables in which the correspondence relationship among the momentum P, the rising frequency, and the voltage amplitude is individually determined. Here, the correspondence relationship is related to each of the ejection tube section types of the ejection tube section 50 which can be mounted in the main body section 40. The momentum conversion tables 671a1, 671a2, 671a3, and so forth are not exemplified herein. However, the momentum conversion tables 671a1, 671a2, 671a3, and so forth are the momentum conversion tables determined for each of the ejection tube section types, and the form thereof is similar to that of the momentum conversion table 671a.

FIG. 19 is a diagram illustrating an example of the data configuration of the momentum conversion table 671a in Exemplary Embodiment 2, and exemplifies the momentum conversion table 671a for the ejection tube section ID of "ID_001". As illustrated in FIG. 19, the momentum conversion table 671a is a data table in which the ejection tube section ID, the dial position (the graduated scale) of the repetitive frequency dial 713, the repetitive frequency instruction value allocated for the dial position, the dial position of the momentum dial 711, the momentum instruction value allocated for the dial position, the dial position of the rising frequency dial 715a, the rising frequency instruction value allocated for the dial position, and the voltage amplitude are associated with each other. The correspondence relationship among the momentum P, the voltage amplitude, and the rising frequency is set for each of the repetitive frequencies.

For example, when the ejection tube section ID read out from the ejection tube side retainer 59 by the reader 47 is "ID_001", the ejection tube section type acquisition unit 651a acquires the momentum conversion table 671a of FIG. 19 as the fitted correspondence relationship (the fitted momentum conversion table 671a) from the momentum conversion tables 671a, 671a1, 671a2, 671a3, and so forth which are determined for each of the ejection tube section types. In this case, the rising frequency setting unit 653a reads out the rising frequency instruction value corresponding to the dial position of the rising frequency dial 715a in the midst of selection from the fitted momentum conversion table 671a and sets the rising frequency. When the rising frequency dial 715a is operated, the rising frequency setting unit 653a reads out the rising frequency instruction value of the selected dial position from the fitted momentum conversion table 671a, thereby updating the setting of the rising frequency. The voltage amplitude setting unit 654a reads out the voltage amplitude corresponding to the combination of each of the dial positions of the momentum dial 711, the repetitive frequency dial 713, and the rising frequency dial 715a in the midst of selection from the fitted momentum conversion table 671a, thereby performing the setting. When any one of the momentum dial 711, the repetitive frequency dial 713, and the rising frequency dial 715a is operated, the voltage amplitude setting unit 654a reads out the voltage amplitude corresponding to the combination of the dial positions of each of dials 711, 713, and 715a from the fitted momentum conversion table 671a, thereby updating the setting.

Flow of Processing

Figure 20:
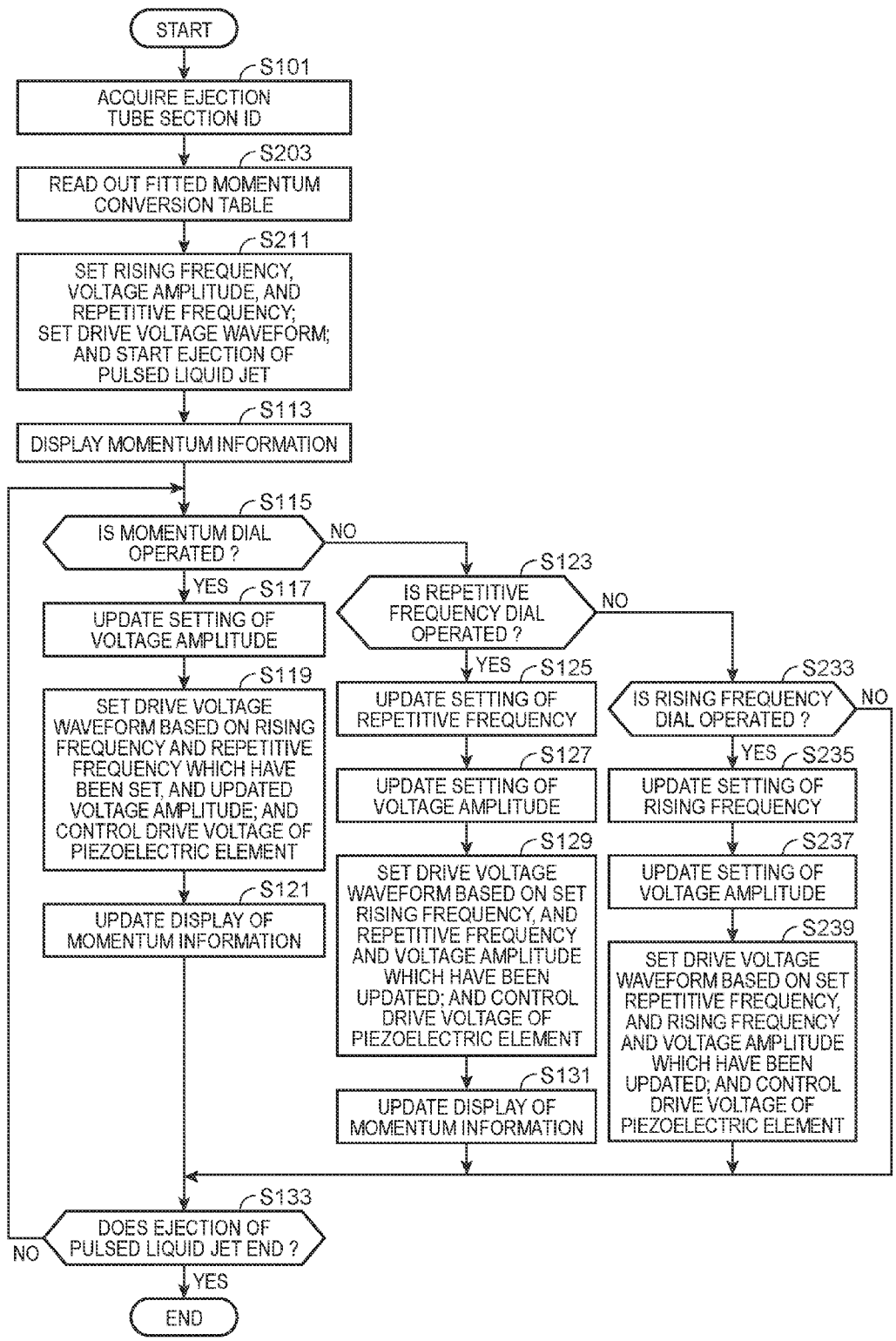
FIG. 20 is a flow chart illustrating a flow of processing performed by a control unit at the time of ejection of a pulsed liquid jet in Exemplary Embodiment 2.

FIG. 20 is a flow chart illustrating a flow of processing performed by the control unit 65a at the time of ejection of a pulsed liquid jet. The same reference numerals and signs will be applied to the processing steps similar to those in FIG. 16.

In Exemplary Embodiment 2, in Step S203, the ejection tube section type acquisition unit 651a reads out the fitted momentum conversion table of the ejection tube section ID acquired in Step S101 from the momentum conversion tables 671a, 671a1, 671a2, 671a3, and so forth for each of the ejection tube section types stored in the storage unit 67.

Then, in Step S211, the rising frequency setting unit 653a reads out the rising frequency instruction value allocated for the dial position of the rising frequency dial 715a in the midst of selection from the fitted momentum conversion table, thereby setting the rising frequency.

In Step S233, the operation of the rising frequency dial 715a is monitored. Then, when the rising frequency dial 715a is operated (Step S233: YES), the rising frequency setting unit 653a reads out the rising frequency instruction value allocated for the selected dial position from the fitted momentum conversion table, thereby updating the setting of the rising frequency (Step S235). Subsequently, the voltage amplitude setting unit 654a reads out the voltage amplitude corresponding to the selected dial position of the rising frequency dial 715a and the combination of each of the dial positions of the momentum dial 711 and the repetitive frequency dial 713 in the midst of selection from a fitted momentum conversion table a, thereby updating the setting of the voltage amplitude (Step S237). Thereafter, the piezoelectric element control unit 652a sets the drive voltage waveform in accordance with the repetitive frequency, the rising frequency and the voltage amplitude which have been set, and applies the drive signal of the set drive voltage waveform to the piezoelectric element 43. (Step S239).

According to Exemplary Embodiment 2, in the liquid ejection device 30, the correspondence relationship (the momentum conversion tables 671a, 671a1, 671a2, 671a3, and so forth for each of the ejection tube section types) among the momentum P, the rising frequency, and the voltage amplitude is determined in advance for each of the repetitive frequencies with respect to each of the ejection tube section types of the ejection tube section 50 which can be mounted in the main body section 40. In this manner, even though the rising frequency is raised or lowered, the drive voltage waveform of the piezoelectric element 43 can be controlled so as to cause the momentum P to be the momentum instruction value.

Modification Example

Hereinbefore, embodiments regarding two Exemplary Embodiments are described. However, a form which can be applied to the invention is not limited to the above-described forms. For example, in the embodiments described above, the momentum conversion tables are stored in the storage unit 67 of the liquid ejection control device 60, and the fitted momentum conversion table of the ejection tube section ID allocated for the ejection tube section 50 which is mounted in the main body section 40 is used while being under control performed by the piezoelectric element 43. In contrast, the fitted momentum conversion table is not limited to the configuration of being read out from the storage unit 67 of the liquid ejection control device 60.

For example, the fitted momentum conversion table may be configured to be acquired from the external server apparatus 100 which stores and manages the momentum conversion table for each of the ejection tube section ID. In this case, the ejection tube section type acquisition units 651 and 651a transmit a transmission request of the momentum conversion table to the server apparatus 100 together with the ejection tube section ID acquired in Step S101 of FIG. 16 or 20. In response thereto, the server apparatus 100 performs transmission processing of the momentum conversion table of the ejection tube section ID which is notified together with the transmission request, with respect to the liquid ejection control device 60. The ejection tube section type acquisition units 651 and 651a may acquire the fitted momentum conversion table from the server apparatus 100 in this manner.

When the momentum conversion table of the ejection tube section ID read out from the ejection tube side retainer 59 by the reader 47 is not stored in the storage unit 67, the fitted momentum conversion table may be configured to be acquired by sending inquiries to the server apparatus 100.

Figure 21:
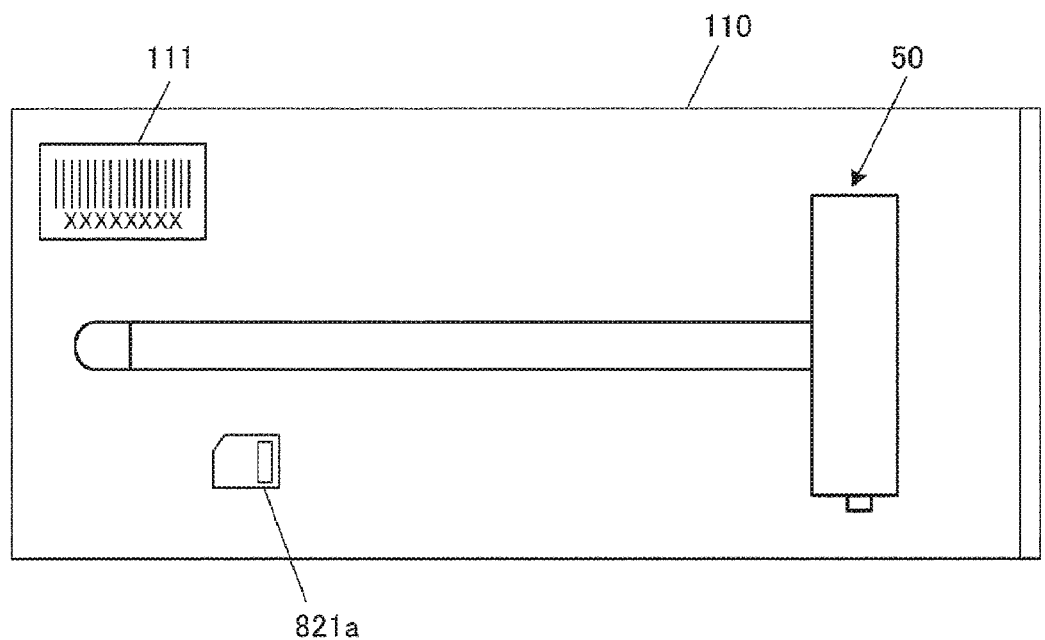
FIG. 21 is a diagram illustrating an example of a packing bag in which an ejection tube section is contained at the time of shipment.

An ejection tube side retainer may be configured to be included together in a packing bag or a packing box in which the ejection tube section 50 is contained at the time of shipment, or may be configured to be bonded on the outer surface. FIG. 21 is a diagram illustrating an example of a packing bag 110. In the packing bag, the ejection tube section 50 is contained, and a memory card 821a storing the fitted momentum conversion table fitting the ejection tube section type is included together. In this case, prior to a surgical operation, the fitted momentum conversion table is read out and acquired from the memory card 821a by the reader/writer 82 of the liquid ejection control device 60.

The ejection tube side retainer 59 as a second retainer may be configured to store the fitted momentum conversion table. In this case, the reader 47 as a second reader reads out the fitted momentum conversion table from the ejection tube side retainer 59, and the ejection tube section type acquisition units 651 and 651a acquire the fitted momentum conversion table read out from the above-described reader 47.

The momentum conversion table may be configured to be stored in the main body side retainer 49. In this case, the ejection tube section type acquisition units 651 and 651a read out the momentum conversion table of the ejection tube section ID which is read out from the ejection tube side retainer 59 by the reader 47, from the main body side retainer 49, thereby acquiring the fitted momentum conversion table.

The embodiments described above exemplify the configuration in which the ejection tube side retainer 59 is included in a suitable place in the ejection tube section 50. However, the ejection tube side retainer may be included in the packing bag or the packing box in which the ejection tube section 50 is contained at the time of shipment. For example, the ejection tube side retainer 59 may be a graphic code, and as illustrated in FIG. 21, an information code 111 such as a bar code or a two-dimensional code in which the ejection tube section ID is encoded may be displayed (be printed, or pasted with a seal paper or the like printed) on the surface of the packing bag 110. The information code 111 is read out by the code reader 85 of the liquid ejection control device 60. The reading-out of the information code 111 performed by the code reader 85 is performed when the ejection tube section 50 is taken out from the packing bag 110 or the like and is mounted in the main body section 40. The code reader 85 reads out and interprets the information code 111, thereby outputting the ejection tube section ID to the control unit 65. In this case, the ejection tube section type acquisition units 651 and 651a acquire the ejection tube section ID from the code reader 85.

Otherwise, in place of the information code 111, the IC tag storing the ejection tube section ID may be configured to be pasted or included together in the packing bag 110 while acquiring the ejection tube section ID read out from the IC tag by the IC tag reader (not illustrated) provided in the liquid ejection control device 60.

In place of the type information of the ejection tube section 50 such as the ejection tube section ID, the ejection tube section type may be configured to be discriminated by acquiring the shape information of the ejection tube section 50. For example, the ejection tube section type acquisition units 651 and 651a acquire image data from the image capturing unit 64 as the shape information of the ejection tube section 50. In this case, a user performs an operation for capturing an image of the appearance of the ejection tube section 50 by using the image capturing unit 64 before the ejection tube section 50 is taken out from the packing bag 110 or the like and is mounted in the main body section 40. First, the ejection tube section type acquisition units 651 and 651a perform image processing of the image data acquired as the shape information, thereby extracting the outer shape of the ejection tube section 50. Then, with reference to the ejection tube section discrimination table 673, an outer shape which coincides with the extracted outer shape is specified from the outer shapes set as the shape condition, and thus, the ejection tube section ID thereof is acquired.

The ejection tube section type may be discriminated by acquiring the weight information of the ejection tube section 50. For example, the ejection tube section type acquisition units 651 and 651a acquire the measurement value from the gravimeter 86 as the weight information of the ejection tube section 50. In this case, the user performs an operation for measuring the weight of the ejection tube section 50 by using the gravimeter 86 before the ejection tube section 50 is taken out from the packing bag 110 or the like and is mounted in the main body section 40. With reference to the ejection tube section discrimination table 673, the ejection tube section type acquisition units 651 and 651a specify a weight which coincides with the acquired weight information from the weights set as the weight condition, thereby acquiring the ejection tube section ID.

Both the shape information and the weight information may be used so as to acquire the ejection tube section ID of which the acquired shape information coincides with the shape condition thereof and the acquired weight information coincides with the weight condition thereof. The ejection tube section ID may be configured to be manually input via the operation units 61 and 61a.

In the embodiments described above, description is given regarding a case where the increasing/decreasing operation of the momentum P is performed in stages by using the momentum dial 711, a case where the increasing/decreasing operation of the repetitive frequency is performed in stages by using the repetitive frequency dial 713, and a case where the increasing/decreasing operation of the rising frequency is performed in stages by using the rising frequency dial 715a. In contrast, each of the dials 711, 713, and 715a may be configured to be able to adjust the momentum instruction value, the repetitive frequency instruction value, and the rising frequency instruction value with no stage even at the position (an intermediate position) between the dials where the graduated scale is marked.

As the specified processing, for example, while paying attention to the momentum dial 711, when a dial position is selected between the graduated scales, with reference to the momentum conversion tables 671, 6711, 6712, 6713, and so forth (for example, FIG. 14) or the momentum conversion tables 671a, 671a1, 671a2, 671a3, and so forth (for example, FIG. 19), momentum instruction values in association with the dial positions of the graduated scales before and after the selected momentum P, and the voltage amplitudes corresponding to the momentum instruction values are read out. Then, linear interpolation is performed by using each of the read out voltage amplitudes, thereby specifying the voltage amplitude corresponding to the currently selected momentum P between the dial positions.

In order to further enhance the accuracy, the voltage amplitudes corresponding to not only the dial positions (the momentum instruction values) of the graduated scales before and after the selected momentum P but also the dial positions thereof further ahead and behind may be read out. Then, each of the read out voltage amplitudes may be used for performing interpolation such as polynomial interpolation so as to specify the voltage amplitude corresponding to the momentum P between the currently selected dial positions.

When a position between the dials (an intermediate position) of the repetitive frequency dial 713 or the rising frequency dial 715a is selected, the voltage amplitude can also be specified by performing similar interpolation.

In the embodiments above, as described with reference to FIG. 10A, the falling shape is variably set in order to raise and lower the repetitive frequency. In contrast, the repetitive frequency may be raised and lowered by simply expanding and contracting the entire drive voltage waveform in the time axis direction. In this case, the simulation which is performed when preparing the momentum conversion tables 671, 6711, 6712, 6713, and so forth or the momentum conversion tables 671a, 671a1, 671a2, 671a3, and so forth is performed while changing the repetitive frequency in the above-described manner.

In the embodiments described above, the rising frequency is exemplified as the rising index value. In contrast, the rising time Tpr may be used in place of the rising frequency.

The momentum dial 711, the repetitive frequency dial 713, the rising frequency dial 715a are not limited to a case where the configuration is realized as the dial switch. For example, the configuration may be realized by a lever switch, a button switch, or the like. The display unit 62 may be formed to be a touch panel and may be realized by a key switch or the like operated by software. In this case, a user performs a touching operation of the touch panel which is the display unit 62, thereby inputting the momentum instruction value, the repetitive frequency instruction value, and the rising frequency instruction value.

In the embodiments above, it is described that the piezoelectric element control units 652 and 652a set the drive voltage waveform in accordance with the rising frequency, the voltage amplitude, and the repetitive frequency which have been set (for example, Steps S111, S119, or the like in FIG. 16). In contrast, the drive voltage waveform for one cycle may be generated in advance with respect to every single combination which can acquire the rising frequency, the voltage amplitude, and the repetitive frequency, thereby storing in the storage units 67 and 77a as the waveform data in association with the corresponding combination. Then, the waveform data corresponding to the combination of the rising frequency, the voltage amplitude, and the repetitive frequency which have been set may be read out, thereby applying the drive signal in accordance with the read out waveform data to the piezoelectric element 43.

The embodiments described above disclose the configuration in which a pulsed liquid jet having the momentum which ranges from 2 nNs to 2 mNs and the kinetic energy which ranges from 2 nJ to 200 mJ is ejected. However, it is preferable to have a configuration in which the pulsed liquid jet having the momentum which ranges from 20 nNs to 200 µNs and the kinetic energy which ranges from 40 nJ to 10 mJ is ejected. In this manner, it is possible to favorably perform excision of living tissues or a gel material.

The entire disclosure of Japanese Patent Application No. 2015-018187 filed Feb. 2, 2015 is expressly incorporated by reference herein.

What is claimed is:

1. A liquid ejection control device which applies a given drive voltage waveform to a piezoelectric element and controls ejection of a pulsed liquid jet from a liquid ejection device which ejects a liquid in a pulsed state by using the piezoelectric element,
   wherein the liquid ejection device has an ejection tube section in which an ejection port of the liquid is formed and which is configured to be attachable/detachable with respect to a main body section including the piezoelectric element, and
   wherein the liquid ejection control device comprises:
      a type discrimination unit that discriminates an ejection tube section type of the ejection tube section;
      a correspondence relationship acquisition unit that acquires a fitted correspondence relationship which fits the discriminated ejection tube section type from correspondence relationships that are set for each of the ejection tube section types while the correspondence relationship is based on a first instruction value related to momentum of the pulsed liquid jet, a second instruction value related to the number of times of ejection of the pulsed liquid jet per unit time, and an index value related to a voltage amplitude of the drive voltage waveform and rising of the drive voltage waveform;
      a first operation unit that inputs the first instruction value;
      a second operation unit that inputs the second instruction value; and
      a voltage amplitude setting unit that sets the voltage amplitude of the drive voltage waveform so as to cause the momentum to meet the first instruction value with reference to the fitted correspondence relationship based on the index value and the second instruction value.

2. The liquid ejection control device according to claim 1, wherein the ejection tube section has a first retainer which retains type information of the ejection tube section, and
   wherein the type discrimination unit acquires the type information from a read-out result of a first reader reading out retained information from the first retainer and discriminates the ejection tube section type.

3. A liquid ejection system, comprising:
   the liquid ejection control device according to claim 2;
   the liquid ejection device; and
   a liquid delivery pump device.

4. The liquid ejection control device according to claim 1, wherein the type discrimination unit acquires at least any one of shape information and weight information of the ejection tube section and discriminates the ejection tube section type.

5. A liquid ejection system, comprising:
   the liquid ejection control device according to claim 4;
   the liquid ejection device; and
   a liquid delivery pump device.

6. The liquid ejection control device according to claim 1,
wherein the ejection tube section has a second retainer which retains the fitted correspondence relationship fitting the ejection tube section type of the ejection tube section, and
wherein the correspondence relationship acquisition unit acquires the fitted correspondence relationship from a read-out result of a second reader reading out retained information from the second retainer.

7. A liquid ejection system, comprising:
the liquid ejection control device according to claim 6;
the liquid ejection device; and
a liquid delivery pump device.

8. The liquid ejection control device according to claim 1, further comprising:
a third operation unit that inputs a third instruction value related to the index value.

9. A liquid ejection system, comprising:
the liquid ejection control device according to claim 8;
the liquid ejection device; and
a liquid delivery pump device.

10. The liquid ejection control device according to claim 1, further comprising:
a falling shape setting unit that variably sets a falling shape of the drive voltage waveform in accordance with the second instruction value.

11. A liquid ejection system, comprising:
the liquid ejection control device according to claim 10;
the liquid ejection device; and
a liquid delivery pump device.

12. The liquid ejection control device according to claim 1, further comprising:
a display control unit that performs controlling to display at least one of the first instruction value and the second instruction value.

13. A liquid ejection system, comprising:
the liquid ejection control device according to claim 12;
the liquid ejection device; and
a liquid delivery pump device.

14. The liquid ejection control device according to claim 1,
wherein the liquid ejection device having momentum of the pulsed liquid jet within a range from 2 [nano-newton seconds (nNs)] to 2 [milli-newton seconds (mNs)] or having the kinetic energy within a range from 2 [nano-joules (nJ)] to 200 [milli-joules (mJ)] is controlled.

15. A liquid ejection system, comprising:
the liquid ejection control device according to claim 14;
the liquid ejection device; and
a liquid delivery pump device.

16. The liquid ejection control device according to claim 1,
wherein the liquid ejection device which excises a living tissue by using the pulsed liquid jet is controlled.

17. A liquid ejection system, comprising:
the liquid ejection control device according to claim 16;
the liquid ejection device; and
a liquid delivery pump device.

18. A liquid ejection system, comprising:
the liquid ejection control device according to claim 1;
the liquid ejection device; and
a liquid delivery pump device.

19. A control method of applying a given drive voltage waveform to a piezoelectric element and controlling ejection of a pulsed liquid jet from a liquid ejection device which ejects a liquid in a pulsed state by using the piezoelectric element,
wherein the liquid ejection device has an ejection tube section in which an ejection port of the liquid is formed and which is configured to be attachable/detachable with respect to a main body section including the piezoelectric element, and
wherein the control method comprises:
discriminating an ejection tube section type of the ejection tube section;
acquiring a fitted correspondence relationship which fits the discriminated ejection tube section type from correspondence relationships that are set for each of the ejection tube section types while the correspondence relationship is based on a first instruction value related to momentum of the pulsed liquid jet, a second instruction value related to the number of times of ejection of the pulsed liquid jet per unit time, and an index value related to a voltage amplitude of the drive voltage waveform and rising of the drive voltage waveform;
inputting the first instruction value;
inputting the second instruction value; and
setting the voltage amplitude of the drive voltage waveform so as to cause the momentum to meet the first instruction value with reference to the fitted correspondence relationship based on the index value and the second instruction value.

* * * * *